United States Patent [19]

Cho et al.

[11] Patent Number: 4,683,234
[45] Date of Patent: * Jul. 28, 1987

[54] 2,6-DIMETHYL-3N,5-DISUBSTITUTED-4-(SUBSTITUTED PHENYL)3,4-DIHYDROPYRIMIDINE COMPOUNDS AND A METHOD FOR TREATING DISORDERS OF CARDIOCIRCULAR SYSTEM

[75] Inventors: Hidetsura Cho, Ibaraki; Kazuo Aisaka, Osaka; Fumio Sato, Nagaokakyo; Takafumi Ishihara, Toyonaka, all of Japan

[73] Assignee: Suntory Limited, Osaka, Japan

[ * ] Notice: The portion of the term of this patent subsequent to Feb. 3, 2004 has been disclaimed.

[21] Appl. No.: 708,885

[22] Filed: Mar. 6, 1985

[30] Foreign Application Priority Data

May 19, 1984 [JP] Japan ................................. 59-101569
May 26, 1984 [JP] Japan ................................. 59-107004
Aug. 3, 1984 [JP] Japan ................................. 59-163614

[51] Int. Cl.[4] .................. A61K 31/505; C07D 239/20
[52] U.S. Cl. ...................................... 514/256; 544/335
[58] Field of Search ........................ 544/335; 514/256

[56] References Cited

U.S. PATENT DOCUMENTS 4,048,171 9/1977 Bossert et al. ........................ 544/335
4,285,955 8/1981 Wehinger et al. .................... 546/321

FOREIGN PATENT DOCUMENTS 0103796 3/1984 European Pat. Off. .
0157219 10/1985 European Pat. Off. .

OTHER PUBLICATIONS

Merck Index, 6352, Nifedipine.
Goerlitzer et al., Chem. Abst. 96-85501u.
Goerlitzer et al., Arch. Pharm. 1981, 314(11), 938–949.
Iwanami et al., Chem. Abst. 86-43570d.
Zidermane et al., Chem. Abst. 75-47266e.
Stoltefuss et al., Chem. Abst. 101-55110 eq. DE 3234684.

Primary Examiner—Donald G. Daus
Assistant Examiner—Cecilia Shen
Attorney, Agent, or Firm—Cushman, Darby & Cushman

[57] ABSTRACT

N-substituted 3,4-dihydropyrimidine derivatives of the formula:

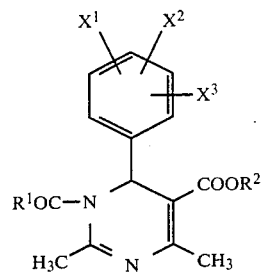

wherein $X^1$, $X^2$ and $X^3$ are the same or different and are hydrogen, nitro, halogen, cyano, trifluoromethyl, methylthio or lower alkoxy;

$R^1$ is $(C_1-C_{13})$ straight or branched alkoxy, $(C_4-C_{12})$ straight or branched alkenyloxy, $(C_5-C_8)$ straight or branched alkynyloxy, $(C_1-C_4)$ straight or branched alkyl, $(C_3-C_6)$ cycloalkyl, —O—$(CH_2)_n$—A wherein n is 1, 2 or 3, A is cyclopropyl, cyclobutyl, cyclopentyl, or $(C_1-C_3)$ haloalkyl, —O—$(CH_2)_m$—O—B wherein m is 1, 2, 3 or 4, B is $(C_1-C_3)$ alkyl, or —O—$(CH_2)_l$—D wherein l is an integer from zero to 8, D is phenyl or substituted phenyl;

$R^2$ is $(C_1-C_{12})$ straight or branched alkyl, $(C_4-C_7)$ straight or branched alkenyl, —$(CH_2)_p$—E wherein p is 1, 2 or 4, E is cyclopropyl, cyclobutyl or cyclopentyl,

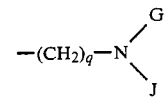

wherein q is 2, 3 or 4, G and J are the same or different and are phenyl, methyl, ethyl, isopropyl, benzyl, phenethyl, methoxycarbonyl or ethoxycarbonyl, or —$(CH_2)_r$—O—L wherein r is 1 or 2, L is methyl, ethyl or phenyl, with the proviso that wherein $R^1$ is methoxy or ethoxy, $R^2$ is neither methyl nor ethyl, and pharmaceutically acceptable acid addition salts thereof are useful as agents for treating disorders of the cardiovascular system, for example, hypotensive agents, agents for ameriolation of brain circulation and anti-angina pectoris agents.

Processes for producing the above compounds economically and effectively are also disclosed.

13 Claims, No Drawings

2,6-DIMETHYL-3N,5-DISUBSTITUTED-4-(SUBSTITUTED PHENYL)3,4-DIHYDROPYRIMIDINE COMPOUNDS AND A METHOD FOR TREATING DISORDERS OF CARDIOCIRCULAR SYSTEM

TECHNICAL FIELD

This invention relates to N-substituted 3,4-dihydropyrimidine derivatives of the formula:

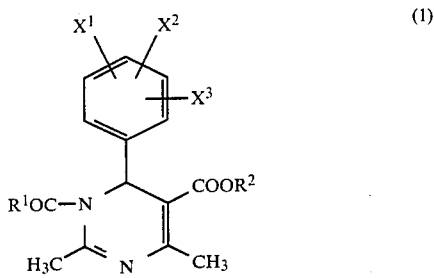

wherein $X^1$, $X^2$ and $X^3$ are the same or different and are hydrogen, nitro, halogen, cyano, trifluoromethyl, methylthio or lower alkoxy; $R^1$ is $(C_1-C_{13})$ straight or branched alkoxy, $(C_4-C_{12})$ straight or branched alkenyloxy, $(C_5-C_8)$ straight or branched alkynyloxy, $(C_1-C_4)$ straight or branched alkyl, $(C_3-C_6)$ cycloalkyl,
—O—$(CH_2)_n$—A wherein n is 1,2 or 3, A is cyclopropyl, cyclobutyl, cyclopentyl or $(C_1-C_3)$ haloalkyl,
—O—$(CH_2)_m$—O—B wherein m is 1,2,3 or 4, B is $(C_1-C_3)$ alkyl, or
—O—$(CH_2)_l$—C wherein l is an integer from zero to 8, D is phenyl or substituted phenyl;
$R^2$ is $(C_1-C_{12})$ straight or branched alkyl, $(C_4-C_7)$ straight or branched alkenyl, —$(CH_2)_p$—E wherein p is 1, 2 or 3, E is cyclopropyl, cyclobutyl or cyclopentyl,

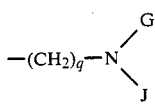

wherein q is 2, 3 or 4, G and J are the same or different and are phenyl, methyl, ethyl, isopropyl, benzyl, phenethyl, methoxycarbonyl or ethoxycarbonyl, or —$(CH_2)_r$—O—L wherein r is 1 or 2, L is methyl, ethyl or phenyl, with the proviso that when $R^1$ is methoxy or ethoxy, $R^2$ is neither methyl nor ethyl, and pharmaceutically acceptable acid addition salts thereof; processes for preparing them; and their use as agents for treating disorders of cardiovascular system. Since the above N-substituted 3,4-dihydropyrimidine derivatives of the formula (1) have strong vasodilation effects and duration of the effects is long, said compounds can be used as agents for treating disorders of the cardio-vascular system, for example, hypotensors, agents for ameriolation of brain circulation and anti-anginapectoris agents.

BACKGROUND ART

Currently it has been found that calcium antagonists ($Ca^{++}$ antagonists) which had been spotlighted as new agents for treating disorders of the cardiovascular system have a variety of pharmacological effects and are active not only against hypertension, angina pectoris, brain circulation and metabolism incompleteness and arrhythmia but also for prevention of arterial sclerosis and increase in effects of carcinostatic agents. Therefore indications as to the benefits of $Ca^{++}$ antagonists continue to increase.

$Ca^{++}$ antagonists which have been known include Nifedipine, Nicardipine, Verapamil, Diltiazem and the like. Up to this day, however, dihydropyrimidine derivatives have not often been investigated. Only a few references disclose said derivatives. (For example refer to Silversmith, E. F. J. Org. Chem., 27, 4090 (1962), Nasipuri, D. et al., Synthesis 1073 (1982), Kashima, C. Tetrahedron Letters 209 (1982) and Japanese Patent Public Disclosure No. 73572/59 (Bayer A.G.).) This can be considered to be due to the instability and tautomerism of the dihydropyrimidine derivatives.

SUMMARY OF THE INVENTION

Since there is room for improevement in the properties of the above mentioned known $Ca^{++}$ antagonists such as duration, organ-selectivity, stability against light, heat etc. and side effects, the inventors eagerly investigated them with a view to creating new $Ca^{++}$ antagonists having improved properties. As a result we found that N-substituted 3,4-dihydropyrimidine derivatives of the formula (1) are excellent in duration and stability and have strong vasodilative effects. We completed this invention on the basis of these observations.

DETAILED DESCRIPTION OF THE INVENTION

This invention provides N-substituted 3,4-dihydropyrimidine of the formula (1) and pharmaceutically acceptable acid addition salts thereof and processes for their production:

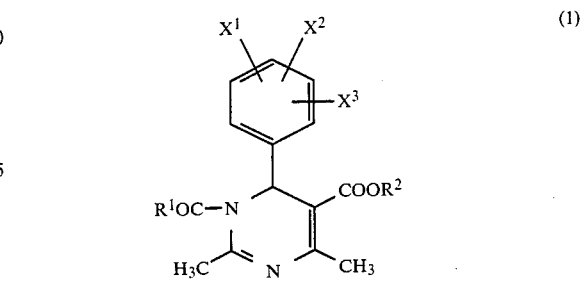

wherein $X^1$, $X^2$, $X^3$, $R^1$ and $R^2$ are as defined above.

Compounds of the formula (1) of this invention are prepared by using dihydropyrimidine derivatives of the formula 2a, b and 2'a, b which are taumeric isomers:

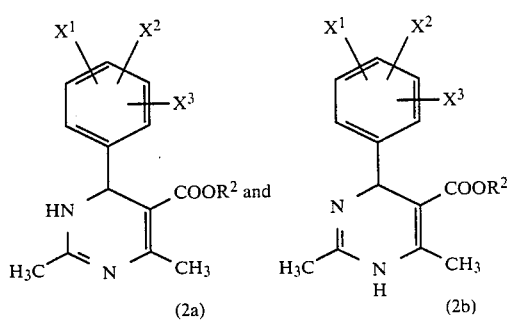

-continued

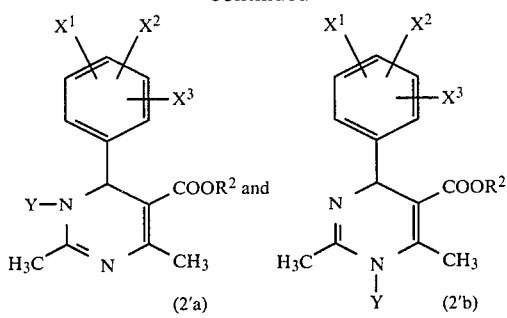

wherein $X^1$, $X^2$, $X^3$, $R^1$ and $R^2$ are as defined above and Y is an alkali metal.

Dihydropyrimidine derivatives of the formula (2a) and (2b) have vasodilative effects too. In order to obtain compounds which are more chemically stable and have stronger effects, compounds of the formula (1) were synthesized. (Refer to Japanese Patent Public Disclosure No. 73572/84.)

The procesures for preparation of dihydropyrimidine derivatives of the formulae 2a, b and 2'a, b are, for example, as follows:

A compound of the formula $R^2OH$ wherein $R^2$ is as defined above and an equivalent of diketene are heated together at 100° C.–200° C., preferably 120° C. for 30–60 minutes (But when $R^2$ is a nitrogen containing roup, the reaction proceeds at 0° C. or room temperature) to produce β-ketoester of the formula (3):

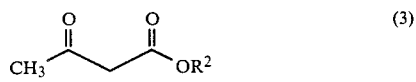

wherein $R^2$ is as defined above.

The compound (3) can also be produced by treating a compound of the formula $R^2OH$, wherein $R^2$ is as defined above, with diketene in the presence of a base at room temperature or 0° C., or by reacting the compound with diketene in the presence of sodium hydride or potassium hydride.

A benzylidene compound of the formula (4):

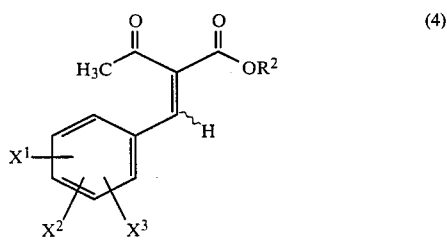

wherein $X^1$, $X^2$, $X^3$ and $R^2$ are as defined above can be obtained by condensation (dehydration) of β-ketoester (3) and arocyclic ring-substituted or unsubstituted benzaldehyde.

The benzylidene compound (4) is condensated with acetamidine or acetamidine hydrochloride to produce a tetrahydropyrimidine compound of the formula:

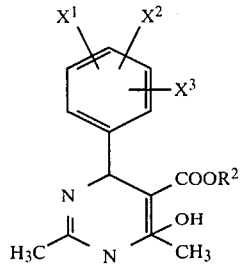

This condensation reaction is carried out in the presence of a base. Preferable bases to be used in this reaction include metal alkoxides and metal halides and preferable solvents are alcohols, ethers and dimethylformamide.

By substituting propylamidine or butylamidine for acetamidine or a salt thereof, tetrahydropyrimidine compounds (5) having ethyl group or propyl group at the position 2 are necessarily produced.

Processes to obtain compounds of the formulae (2a) and 2(b) from compounds of the formula (5) include, for example, (a) a process comprising hydrating a compound (5) by heating with p-toluenesulfonic acid, benzenesulfonic acid or the like; (b) a process comprising mixing a compound (5) with not less than about 5 parts by weight, preferably about 10 parts by weight of an inorganic substance such as alumina, silica gel or molecular sieve, heating the mixture at 120°–200° C. for 15 minutes to 1 hr and extracting the mixture with an organic solvent; and (c) a process comprising dissolving a compound (5) in phosphorus oxychloride and heating the solution to hydrate the compound.

According to processes (a), (b) and (c) the dihydropyrimidine derivatives (2a) and (2b) are obtained in a yield of 40–70%, 20–50% and about 50% respectively. The derivatives can also be obtained by using an acid such as camphor-10-sulfonic acid or a lewis acid such as boron trifluoride ether complex to dehydrate a compound (5).

The product can be purified by conventional methods such as adsorption chromatography, ion-exchange chromatography, partition chromatography, evaporation, recrystallization, etc. Alternatively the product can be crystallized as an inorganic acid salt thereof, such as hydrochloride, sulfate or phosphate or an organic acid salt thereof, such as oxalate, tartarate, succinate or maleate, and then purified by recrystallization.

The thus obtained dihydropyrimidines of the formulae (2) and (2b) which are tautomeric isomers and are disclosed in Patent Public Disclosure No. 73572/84 are converted to the compounds of this invention by using the following processes:

The compound represented by the formulae (2a) and (2b) is dissolved in an organic solvent such as hydrocarbon chloride, aromatic hydrocarbon or ether and is reacted with a carbonylhalide or an acylhalide of the formula

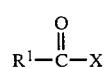

wherein X is halogen, and $R^1$ is ($C_1$–$C_{13}$) straight or branched alkoxy, ($C_4$–$C_{12}$) straight or branched alkenyloxy, (C$_5$-C$_8$) straight or branched alkynyloxy, (C$_1$-C$_4$) straight or branched alkyl (C$_3$-C$_6$) cycloalkyl, —O—(CH$_2$)$_n$—A wherein n is 1, 2 or 3, A is cyclopropyl, cyclobutyl, cyclopentyl or (C$_1$-C$_3$) haloalkyl, —O—(CH$_2$)$_m$—O—B wherein m is 1, 2, 3 or 4, B is (C$_1$-C$_3$) alkyl, or —O—(CH$_2$)$_l$—D wherein l is an integer from zero to 8, D is phenyl or substituted phenyl, or its equivalent, that is, acid anhydride or dialkyl carbonate in the presence of a base e.g. trialkylamine, sodium hydride or potassium hydride.

Alternatively the compound represented by the formulae (2a) and (2b) is converted to an alkali metal salt thereof represented by the formulae (2'a) and (2'b) with sodium hydride, potassium hydride or lithium hydride and is reacted with the compound of the formula

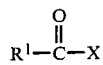

wherein R$^1$ is methyl or ethyl, or its equivalent to produce the compound (1) of this invention. R$^1$ in N-substituent at the position 3 of the N-substituted 3,4-dihydropyrimidine derivatives (1) which can be synthesized according to the above methods includes, for example, methoxy, ethoxy, n-propoxy, isopropoxy, n-butoxy, sec-butoxy, t-butoxy, iso-butoxy, n-pentyloxy, methylbutoxy, ethylpropoxy, n-hexyloxy, methylpentyloxy, ethylbutoxy, n-heptyloxy, methylhexyloxy, ethylpentyloxy, n-octyloxy, methylheptyloxy, ethylhexyloxy, n-nonyloxy, methyloctyloxy, ethylheptyloxy, n-decanyloxy, methylnonyloxy, ethylothyloxy, cyclopropylmethyloxy, cyclopropylethyloxy, cyclopropylopropyloxy, trichloroethoxy, trichloropropoxy, benzyloxy, aromatic ring substituted benzyloxy, methoxyethoxy, ethoxyethoxy, propoxyethoxy, dichloroethoxy, ethoxypropoxy, dimethylbutoxy, dimethylpentyloxy, dimethylhexyloxy, dimethylheptyloxy, dimethyloctyloxy, undecanyloxy, methyldecanyloxy, ethylnonyloxy, dimethylnonyloxy, cyclobutylmethoxy, cyclobutylethoxy, methoxypropoxy, methoxybutoxy, ethoxybutoxy, propoxypropoxy, phenylbutoxy, phenylpentyloxy, phenylhexyloxy, dodecanyloxy, tridecanoyloxy, cyclopropylethoxy, cyclopropylpropoxy, 2-butenyloxy, 4-octenyloxy, 3-methyl-2-octenyloxy, geranyloxy, 2-decenyloxy, 3,7-dimethyl-2-decenyloxy, 3-ethyl-7-methyl-2-decenyloxy, 4-pentynyloxy, 2-hexynyloxy, 2-heptynyloxy, 6-methyl-2-heptynyloxy, 3-heptynyloxy, 4-ethoxycarbonylphenyloxy, 4-propoxycarbonylphenyloxy, 3,4-dichlorophenyloxy, 3,4-dinitrophenyloxy, 4-nitrophenyloxy, 3-nitrophenyloxy, 4-chlorophenyloxy, 3-chlorophenyloxy, 4-bromophenyloxy, 4-methoxyphenyloxy, 3,4-dimethoxyphenyloxy, 4-ethoxyphenyloxy, phenyloxy, 4-methoxycarbonylphenylmethyloxy, 4-ethoxycarbonylphenylmethyloxy, 2-nitrophenylmethyloxy, 3-nitrophenylmethyloxy, 4-nitrophenylmethyloxy, 3-chlorophenylmethyloxy, 4-chlorophenylmethyloxy, 3,4-dichlorophenylmethyloxy, 4-bromophenylmethyloxy, 3-methoxyphenylmethyloxy, 4-methoxyphenylmethyloxy, 3,4-dimethoxyphenylmethyloxy, 4-propoxycarbonylphenylmethyloxy, benzyloxy, phenethyloxy, 3-methoxyphenylethyloxy, 4-methoxyphenylethyloxy, 3,4-dimethoxyphenylethyloxy, 3-methoxycarbonylphenylethyloxy, 4-ethoxycaronylphenylethyloxy, 4-methoxycarbonylphenylethyloxy, 3,4-dimethoxycarbonylphenylethloxy, 3-chlorophenylethyloxy, 4-chlorophenylethyloxy, 3,4-dichlorophenylehyloxy, 4-bromophenylethloxy, 3,4-dibromophenylethyloxy, 3-nitrophenylethyloxy, 4-nitrophenylethyloxy, 3,4-dinitrophenylethyloxy, phenylpropyloxy, 3-methoxyphenylpropyloxy, 4-methoxyphenylpropyloxy, 3,4-dimethoxyphenylpropyloxy, 3-methoxycarbonylphenylpropyloxy, 4-methoxycarbonylphenylporpyloxy, 4-ethoxycarbonylphenylpropyloxy, 3-chlorophenylpropyloxy, 4-chlorophenylpropyloxy, 3,4-dichlorophenylpropyloxy, 4-bromophenylpropyloxy, 3-nitrophenylpropyloxy, 4-nitrophenylpropyloxy, 3,4-dinitrophenylpropyloxy, phenylbutyloxy, 4-methoxyphenylbutyloxy, 3-ethoxyphenylbutyloxy, 3,4-dimethoxyphenylbutyloxy, 4-chlorophenylbutyloxy, 3,4-dichlorophenylbutyloxy, 4-methoxycarbonylphenylbutyloxy, 4'-nitrophenylbutyloxy, 3,4-dinitrophenylbutyloxy, phenylpentyloxy, 4-methoxyphenylpentyloxy, 4-ethoxyphenylpentyloxy, 3,4-dimethoxyphenylpentyloxy, 4-chlorophenylpentyloxy, 3,4-dichlorophenylpentyloxy, 4-nitrophenylpentyloxy, 3,4-dinitrophenylpentyloxy, phenylhexyloxy, 4-methoxyphenylhexyloxy, 4-methoxycarbonylphenylhexyloxy, 4-chlorophenylhexyloxy, 3,4-dichlorophenylhexyloxy, 4-nitrophenylhexyloxy, 3,4-dinitrophenylhexyloxy, phenylheptyloxy, 3-methoxyphenylheptyloxy, 4-chlorophenylheptyloxy, 3,4-dichlorophenylheptyloxy, 4-nitrophenylheptyloxy, phenyloctyloxy, 4-methoxyphenyloxtyloxy, 4-chlorophenyloctyloxy, 3,4-dichlorophenyloctyloxy, 4-nitrophenyloctyloxy, 3,4-dinitrophenyloctyloxy, methyl, ethyl, propyl, isopropyl, cyclopropyl, n-butyl, sec-butyl, isobutyl, t-butyl, pentyl, methylbutyl, hexyl, methylpentyl, hepty, methylhexyl, octyl, methylheptyl, nonyl, methylnonyl, methyloctyl, decanyl, cyclopropyl and cyclobutyl.

And the substituent at the position 5, R$^2$ includes cyclopropylmethyl, cyclopropylethyl, cyclobutylmethyl, cyclobutylethyl, methylphenylaminoethyl, ethylphenylaminoethyl, methylphenylaminopropyl, methylphenylaminobutyl, ethylphenylaminobutyl, diphenylaminoethyl, dimethylaminoethyl, dimethylaminopropyl, methylbenzylaminoethyl ethylbenzylaminoethyl, methylbenzylaminopropyl, ethylbenzylaminopropyl, methylbenzylaminobutyl, methylphenethylaminoethyl, methylmethoxycarbonylaminoethyl, ethylmethoxycarbonylaminoethyl, methylmethoxycarbonylaminopropyl, methylethoxycarbonylaminoethyl, ethylethoxycarbonylaminoethyl, methylisopropylaminoethyl, diisopropylaminoethyl, methoxymethyl, ethoxymethyl, phenoxymethyl, ethoxymethyl, ethoxyethyl, phenoxyethyl, methyl, ethyl, propyl, isopropyl, butyl, isobutyl, secbutyl, t-butyl, pentyl, 3-methylbutyl, 2-methylbutyl, hexyl, 4-methylpentyl, 3-methylpentyl, 2-ethylbutyl, heptyl, 5-methylhexyl, 4-methylhexyl, 3-ethylpentyl, octyl, 6-methylheptyl, 4-ethylhexyl, 3,3-dimethylhexyl, 2-butenyl, 3-butenyl, 3-pentenyl, 3-methyl-2-butenyl, 2-pentenyl, 2-hexenyl, 3-hexenyl, 4-methyl-3-hexenyl, 3-methyl-2-hexenyl, 2-heptenyl, 3-methyl-2-hexenyl, 5-methyl-4-hexenyl, cyclopropylmethyl, cyclopropylethyl, cyclopropylpropyl, cyclobutylmethyl, cyclobutylethyl, cyclopentylmethyl, cyclopentylethyl, cyclopentylpropyl and the like.

After the above reaction, the products of the formula (1) of this invention can be purified by using conventional methods such as adsorption column chromatography, ion-exchange chromatography or recrystallization. Alternatively, the products can be treated with an inorganic acid such as hydrochlorin acid, sulfuric acid or phosphoric acid, or an organic acid such as oxalic acid, succinic acid or malic acid to convert them to salts thereof and then can be purified by recrystallization, adsorption chromatography or ion-exchange chromatography.

The thus obtained compound of the formula (1) of this invention should long-term duration, strong vasodilative and hypotensive effects in pharmacological tests according to Langendorff's method and others wherein anesthetized dogs were used.

That is, the compounds of this invention have excellent coronary-vasodilative effects in guinea pigs and improve blood circulation through the vertebral arteries of dogs and reduce the resistance of vertebral arteries and systemic blood pressure in dogs.

Thus, the compounds are useful as agents for treating coronary impairments, brain circulation incompetence and hypertension.

The compounds (1) of this invention can be administered alone or in combination with excipients in a variety of dosage forms such as tables, troches, pills, granules, powders, capsules, ampules, suppositories and the like. The excipients include, for example, starch, dexstrin, sucrose, lactose, silic acid, carboxymethylcellulose, cellulose, geratin, polyvinylpyrrolidone, glycerin, agar, calcium carbonate, sodium bicarbonate, paraffin, cetyl alcohol, stearic acid esters, kaolin, bentonite, talc, calcium stearate, magnecium stearate, polyethyleneglycol, water, ethanol, isopropyl alcohol, propyleneglycol and the like.

For parenteral administration, the compounds of this invention are connected into water soluble salts thereof and the salts are dissolved in sterile distilled water or sterile physiological saline and are filled in ampules to be used for injection. If necessary, stabilizing agents and/or buffering agents can be included in the ampules.

For oral administration, optimum dose range of the compound (1) of this invention is 5-500 mg per day. Of course, this dose range can be suitably changed depending upon the characteristics of the subjects including age, response, weight, severity of disease etc.

The present invention is illustrated by the following examples. However, it should be understood that the invention is not limited to the specific detailes of these examples. Unless otherwise specified, all specified temperatures are in °C.

The compounds of this invention shown in the following examples can easily be converted to salts thereof by dissolving them in a suitable solvent, for example, an ether or an alcohol, and treating the solution with a solution of an inorganic or organic acid at room temperature.

EXAMPLE 1

5-Ethoxycarbonyl-2,6-dimethyl-4-(2-nitrophenyl)-3N-octyloxycarbonyl-3,4-dihydropyrimidine 172 mg of 60% Suspension of sodium hydride in oil (4.3 millimole) was in parts added to a solution of 1.0 g (3.3 millimole) of 5-ethoxycarbonyl-2,6-dimethyl-4-(2-nitrophenyl)dihydropyrimidine in 30 ml of anhydrous tetrahydrofuran at 0° C. and then 9.8 ml (50 millimole) of n-octyl chloroformate was added. The reaction solution was stirred at room temperature for 45 minutes and concentrated under reduced pressure to about half volume. Water was added to the concentrate and it was extracted with chloroform. The organic phase was washed with saturated NaCl solution, dried over magnesium sulfate and evaporated under reduced pressure to obtain the residue.

After the residue was purified on silica gel by column chromatography (eluant: chloroform) to obtain 1.5 g (99% yield) of title compound.

EXAMPLE 2

5-Ethoxycarbonyl-2,6-dimethyl-4-(2-nitrophenyl)-3-N-(2,2,2-trichloroethyoxycarbonyl)-3,4-dihydropyrimidine 1.0 g (3.3 millimole) of 5-Ethoxycarbonyl-2,6-dimethyl-4-(2-nitrophenyl)dihydropyrimidine was dissolved in 20 ml of chloroform and 2 ml of triethyl amine (14.3 millimole) was added to the solution with stirring and then 0.9 ml (6.54 millimole) of 2,2,2-trichloroethoxychloroformate was added dropwise. After stirring for one hour, the reaction mixture was concentrated under reduced pressure and the residue was purified on silica gel by column chromatography (eluant: methylene chloride) to obtain 0.71 g (45% yield) of title compound.

EXAMPLE 3

3-N-cyclopropylmethoxycarbonyl-2,6-dimethyl-5-ethoxycarbonyl-4-(2-nitrophenyl)-3,4-dihydropyrimidine 408 mg of 50% Suspension of sodium hydride in oil (8.5 millimole) was suspended in 4 ml of anhydrous tetrahydrofuran. To the suspension a solution of 612 mg (8.5 millimole) of cyclopropylcarbinol in 4 ml of anhydrous tetrahydrofuran was added at 0° C. and the solution was stirred at room temperature for ten minutes. To the solution 0.5 ml (4.2 millimole) of trichloromethyl chloroformate (phosgene dimer) was slowly added dropwise and the mixture was further stirred at room temperature for twenty five minutes.

On the other hand, 45 mg of 50% suspension of sodium hydride (0.94 millimole) in oil was suspended in 3 ml of anhydrous tetrahydrofuran. To the suspension 259 mg (0.85 millimole) of 5-ethoxycarbonyl-2,6-dimethyl-4-(2-nitrophenyl)dihydropyrimidine in 5 ml of tetrahydrofuran was added dropwise with stirring. The mixture was stirred for further 5 minutes. To the solution the above reaction mixture of the above sodium hydride, cyclopropylcarbinol and trichloromethyl chloroformate was added at 0° C. After 15 minutes, saturated NaCl solution was added to the mixture and it was extracted with chloroform. The organic phase was dried over anhydrous magnesium sulfate and concentrated. The residue was purified on silica gel by thin layer chromatography (developer: chloroform/methanol 10:1) to obtain 122 mg (36% yield) of title compound.

EXAMPLES 4-14

By using the process described in Example 1, products as shown in the following table were obtained from apropriate starting compounds.

Yield data and physicochemical data identifying the products are shown in Table 1.

TABLE 1

![Structure: phenyl ring with X¹, X², X³ substituents, CH(N(C(O)OR¹))–C(=CO₂R²)–N=C(CH₃)–CH₃ chain]

| Ex. No. | Compound | Yield (%) | Properties (Recrystallization solvents) | IR spectrum (CHCl₃, cm⁻¹) | NMR spectrum (CDCl₃, δ) | Ⓐ Ⓑ | High resolution mass spectrum Analysis |
|---|---|---|---|---|---|---|---|
| 1 | R¹=n-octyloxy R²=ethyl X¹=2-nitro X²,X³=H | 99 | oil | 1730, 1705 | 0.88(3H,t,J=7Hz), 1.23(3H,t,J=7Hz), 1.2–1.3(10H,m), 1.6–1.7(2H,m), 2.36(3H,s), 2.46(3H,s), 4.14(2H,t,J=7Hz), 4.17(2H,q,J=7Hz), 6.87(1H,s), 7.4–7.8(4H,m) | Ⓐ | Calculated for C₂₄H₃₃N₃O₆: 459.5448 Found: 459.5450 |
| 2 | R¹=2,2,2-trichloroethoxy R²=ethyl X¹=2-nitro X², X³=H | 45 | m.p. 115–117° (benzene.hexane) | 1750, 1710 (determined by KBr method) | 1.23(3H,t,J=7Hz), 2.40(3H,s), 2.47(3H,s), 4.15(2H,q,J=7Hz), 4.67(1H,d,J=12Hz), 5.00(1H,d,J=12Hz), 6.90(1H,s), 7.23–7.80(4H,m) | Ⓐ | Calculated for C₁₈H₁₈N₃O₆Cl₃: 4718.7184 Found: 478.7190 |
| 3 | R¹=cyclopropylmethoxy R²=ethyl X¹=2-nitro X²=X³=H | 36 | m.p. 97–98° (ether.hexane) | 1720, 1700 | 0.25–0.40(2H,m), 0.55–0.65(2H,m), 1.05–1.20(1H,m), 1.23(3H,t,J=7Hz), 2.36(3H,s), 2.46(3H,brS), 3.85–4.25(4H,m), 6,89(1H,brS), 7.38–7.80(4H,m) | Ⓐ | Calculated for C₂₀H₂₃N₃O₆: 401.1539 Found: 401.1526 |
| 4 | R¹=n-propyloxy R²=ethyl X¹=2-nitro X²=X³=H | 91 | m.p. 78.2–79.2° (ether.hexone) | 1730, 1705 | 0.94(3H,t,J=7Hz), 1.23(3H,t,J=7Hz), 1.73(2H,tq,J=7Hz), 2.35(3H,s), 2.45(3H,s), 4.11(2H,t,J=7Hz), 4.13(2H,q,J=7Hz), 6.88(1H,s), 7.4–7.8(4H,m) | Ⓐ | Calculated for C₁₉H₂₄N₃O₆: 390.4180 Found: 390.4183 |
| 5 | R¹=2-methylpropyloxy R²=ethyl X¹=2-nitro X²=X³=H | 99 | oil | 1720, 1705 | 0.92(6H,d,J=7Hz), 1.24(3H,t,J=7Hz), 1.9–2.1(1H,m), 2.36(3H,s), 2.46(3H,s), 3.98(1H,d,J=7Hz), 4.00(1H,d,J=7Hz), 4.16(2H,d,J=7Hz), 6.90(1H,s), 7.4–7.8(4H,m) | Ⓐ | Calculated for C₂₀H₂₅N₃O₆: 403.4370 Found: 403.4371 |
| 6 | R¹=n-butoxy R²=ethyl X¹=2-nitro X²=X³=H | 96 | m.p. 101–103° (as HCl salt methanol.ether) | 1720, 1700 | 0.94(3H,t,J=7Hz), 1.23(3H,t,J=7Hz), 1.3–1.4(2H,m), 1.67(2H,tt,J=7Hz), 2.34(3H,s), 2.45(3H,s), 4.15(2H,t,J=7Hz), 4.18(2H,q,J=7Hz), 6.87(1H,s), 7.3–7.8(4H,m) | Ⓐ | Calculated for C₂₀H₂₅N₃O₆: 403.4370 Found: 403.4368 |
| 7 | R¹=n-penthloxy R²=ethyl X¹=2-nitro X²=X³=H | 90 | m.p. 85–95° (as HCl salt acetone ether) | 1770, 1710 (determined by KBr method) | 0.88(3H,t,J=7Hz), 1.24(3H,t,J=7Hz), 1.20–1.35(4H,m), 1.70(2H,tt,J=7Hz), 2.76(3H,s), 3.11(3H,s) 4.11–4.39(4H,m), 7.13(1H,s), 7.52–7.95(4H,m) | Ⓐ | Calculated for C₂₁H₂₇N₃O₆: 417.4640 Found: 4.174620 |
| 8 | R¹=n-hexyloxy R²=ethyl | 99 | oil | 1720, 1700 | 0.88(3H,br.t,J=7Hz), 1.23(3H,t,J=7Hz), 1.20–1.45(8H,m), | Ⓐ | Calculated for C₂₂H₂₉N₄O₆: 431.4909 |

TABLE 1-continued

[Structure: phenyl ring with X¹, X², X³ substituents attached to a CH bearing CO₂R² group, connected via N-C(=O)-R¹ amide and C=N-C(CH₃) oxime portion]

| Ex. No. | Compound | Yield (%) | Properties (Recrystallization solvents) | IR spectrum (CHCl₃, cm⁻¹) | NMR spectrum (CDCl₃, δ) | | High resolution mass spectrum Analysis |
|---|---|---|---|---|---|---|---|
| | $X^1$=2-nitro $X^2$=$X^3$=H | | | | 1.50–1.85(2H,m), 2.35(3H,s), 2.45(3H,brs), 4.00–4.35(4H,m), 6.87(1H,s), 7.35–7.90(4H,m) | Ⓐ Ⓑ | Found: 431.4919 |
| 9 | $R^1$=ethylhexyloxy $R^2$=ethyl $X^1$=2-nitro $X^2$=$X^3$=H | 63 | oil | 1720 | 0.88(6H,brt,J=7Hz), 1.20–1.40 (11H,m), 1.60–1.75(1H,m), 2.33(3H,s), 2.46(3H,brs), 3.90–4.25(4H,m), 6.88(1H,s), 7.35–7.80(4H,m) | Ⓐ | Calculated for C₂₄H₃₃N₃O₆: 459.2368 Found: 459.2373 |
| 10 | $R^1$=2-(methoxy)ethoxy $R^2$=ethyl $X^1$=2-nitro $X^2$=$X^3$=H | 48 | m.p. 117–118° (as HCl salt ethanol, ether) | 1730, 1710 | 1.23(3H,t,J=7Hz), 2.35(3H,s), 2.45(3H,d,J=0.8Hz), 3.37(3H,s), 3.55–3.72(2H,m), 4.05–4.25(3H,m), 4.40–4.50(3H,m) | Ⓑ | Calculated for C₁₉H₂₄ClN₃O₇ (HCl salt): C(%) 51.64 H(%) 5.48 N(%) 9.51 Found: 51.81 5.34 9.62 |
| 11 | $R^1$=benzyloxy $R^2$=ethyl $X^1$=2-nitro $X^2$=$X^3$=H | 64 | oil | 1730, 1710 | 1.22(3H,t,J=7Hz), 2.30(3H,s), 2.43(3H,s), 4.10–4.20(2H,m), 5.11(1H,d,J=12Hz), 5.28(1H,d, J=12Hz), 6.87(1H,s), 7.34–7.78(4H,m) | Ⓐ | Calculated for C₂₃H₂₃N₃O₆: 437.4547 Found: 437.4550 |
| 12 | $R^1$=n-heptyloxy $R^2$=ethyl $X^1$=2-nitro $X^2$=$X^3$=H | 86 | oil | 1730, 1710 | 0.88(3H,t,J=7Hz), 1.23(3H,t, J=7Hz), 1.24–1.35(8H,m), 1.64–1.73(2H,m), 2.34(3H,s), 2.45(3H,s) 4.05–4.26(4H,m), 6.87(1H,s), 7.36–7.77(4H,m) | Ⓐ | Calculated for C₂₃H₃₁N₃O₆: 445.2202 Found: 445.2226 |
| 13 | $R^1$=n-heptyloxy $R^2$=i-propyl $X^1$=2-nitro $X^2$=$X^3$=H | 79 | oil | 1730, 1700 | 0.88(3H,t,J=7Hz), 1.07(3H,d, J=6Hz), 1.29(3H,d,J=6Hz), 1.23–1.35(8H,m), 1.64–1.73 (2H,m), 2.32(3H,s), 2.46(3H,s), 4.07–4.28(2H,m), 4.98–5.07(1H, m), 6.87(1H,s), 7.36–7.78(4H,m) | Ⓐ | Calculated for C₂₄H₃₃N₃O₆: 459.2358 Found: 459.2364 |
| 14 | $R^1$=n-heptyloxy $R^2$=n-propyl $X^1$=2-nitro $X^2$=$X^3$=H | 83 | oil | 1730, 1700 | 0.80(3H,t,J=7Hz), 0.88(3H,t, J=7Hz), 1.20–1.38(8H,m), 1.57–1.73(4H,m), 2.33(3H,s), 2.47(3H,s), 4.20–4.30(4H,m), 6.87(1H,s), 7.36–7.77(4H,m) | Ⓐ | Calculated for C₂₄H₃₃N₃O₆: 459.2369 Found: 459.2370 |

EXAMPLE 15

5-Ethoxycarbonyl-2,6-dimethyl-4-(2-nitrophenyl)-3-propionyl-3,4-dihydropyrimidine 1.00 g (3.30 millimole) of 5-Ethoxycarbonyl-2,6-dimethyl-4-(2-nitrophenyl)-dihydropyrimidine was dissolved in 15 ml of chloroform. To the solution, 2 ml of triethylamine (14.3 millimole) was added with stirring and then 0.4 g (4.32 millimole) of propionyl chloride was added dropwise. The mixture was stirred at room temperature for 40 minutes and concentrated under reduced pressure. The residue was purified on silica gel by column chromatography and recrystallized from benzene/hexane to obtain 0.69 g (58% yield) of title compound.

EXAMPLE 16

By using the same procedure was Example 12 except that acetyl chloride was used in place of propionyl chloride, 5-ethoxycarbonyl-2,6-dimethyl-4-(2-nitrophenyl)-3-acetyl-3,4-dihydropyrimidine was obtained.

EXAMPLE 17

3-Cyclopropionyl-5-ethoxycarbonyl-4-(2-nitrophenyl)-2.6-dimethyl-3,4-dihydropyrimidine 0.2 g of 60% Suspension of sodium hydride (5 millimole) in oil was suspended in 10 ml of anhydrous tetrahydrofuran. To the solution 1 g (3.3 millimole) of 5-ethoxycarbonyl-2,6-dimethyl-4-(2-nitrophenyl)-dihydropyrimidine in 10 ml of anhydrous tetrahydrofuran was added at 0° C. and the mixture was stirred for 5 minutes. To this solution 1.1 g (10.5 millimole) of cyclopropylcarbonylchloride dissolved in 10 ml of anhydrous tetrahyrofuran was added at 0° C. and stirred for one hour.

To the reaction solution chloroform was added and the solution was washed with 2% aqueous sodium hydroxide solution and then saturated NaCl solution. The organic phase was dried and concentrated and the residue was purified on silica gel by chromatography (developer:chloroform) to obtain crystals. The crystals were recrystallized from ether to obtain 0.703 g (57% yield) of title compound as light yellow prismatic crystals.

Yield and physicochemical data of the products obtained in Examples 15-17 are shown in Table 2.

TABLE 2

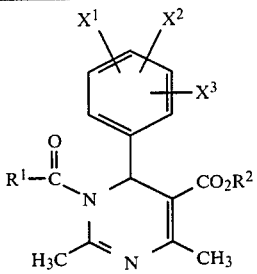

| Ex. No. | Compound | Yield (%) | Properties (Recrystallization solvents) | IR spectrum (CHCl₃, cm⁻¹) | NMR spectrum (CDCl₃, δ) | Ⓐ High resolution mass spectrum Ⓑ Analysis |
|---|---|---|---|---|---|---|
| 15 | $R^1$=ethyl $R^2$=ethyl $X^1$=2-nitro $X^2=X^3$=H | 58 | m.p. 153-155° (benzene.hexane) | 1705, 1690 (determined by KBr method) | 1.18(3H,t,J=7Hz), 1.26(3H,t, J=7Hz), 2.36(3H,s), 2.42(3H,s), (2H,m), 6.84(1H,s), 7.30-7.72(4H,m) | Ⓐ Calculated for $C_{18}H_{21}N_3O_5$: 359.3837 Found: 359.3831 |
| 16 | $R^1$=methyl $R^2$ = ethyl $X^1$=2-nitro $X^2=X^3$=H | 99 | m.p. 105-107° (ether) | 1700 | 1.26(3H,t,J=7Hz), 2.35(3H,s), 2.36(3H,s), 2.44(3H,brS), 4.10-4.30(2H,m), 6.83(1H,brS), 7.32-7.78(4H,m) | Ⓑ Calculated for $C_{17}H_{19}N_3O_5$: C(%) H(%) N(%) 59.12 5.55 12.17 Found: 59.17 5.50 11.97 |
| 17 | $R^1$=cyclopropyl $R^2$=ethyl $X^1$=2-nitro $X^2=X^3$=H | 57 | m.p. 138-139° (ether) | 1700 | 0.95-1.10(3H,m), 1.23(3H,t, J=7Hz), 1.35-1.45(1H,m), 1.78-1.90(1H,m), 2.40(3H,s), 2.47(3H,brS), 4.05-4.25(2H,m), 6.91(1H,s), 7.35-7.80(4H,m) | Ⓑ Calculated for $C_{19}H_{21}N_3O_5$ C(%) H(%) N(%) 61.44 5.70 11.32 Found: 61.25 5.71 10.94 |

EXAMPLE 18

2,6-Dimethyl-3-ethoxycarbonyl-5-(2-N-methoxy-N-benzyl)aminoethoxycarbonyl-4-(2-nitrophenyl)-3,4-dihydropyrimidine (a) 2-(N-methyl-N-benzyl)aminoethanol 4.7 ml (39.5 millimole) of Benzyl bromide was added to a solution of 2.96 g (39.5 millimole) of 2-methylaminoethanol in 15 ml of triethylamine at 0° C. and the reaction mixture was stirred at room temperature for 18 hrs. Water was added to the mixture and it was extracted with chloroform. The organic phase was dried over magnesium sulfate and evaporated under reduced pressure to obtain 5.38 g (83% yield) of 2-(N-methyl-N-benzyl)aminoethanol.

(b) 2-(N-methyl-N-benzyl)aminoethyl acetoacetate 0.47 ml (6.06 millimole) of Diketene was carefully added to 1.0 g (6.06 millimole) of 2-(N-methyl-N-benzyl)aminoethanol chilled at 0° C. with stirring. The reaction completed in an instance to produce 2-(N-methyl-N-benzyl)aminoethyl acetoacetate in a yield of 100%.

(c) 2'-Nitrobenzylidene-2-(N-methyl-N-benzyl)aminoethyl acetoacetate 860 mg (5.7 millimole) of o-nitrobenzaldehyde and 1.4 g (6 millimole) of 2-(N-methyl-N-benzyl)aminoethylacetoacetate were dissolved in 4 ml of benzene. 0.06 ml (0.57 millimole) of Piperidine was added to the solution and the mixture was heated for 15 hrs in a Dean-Stark apparatus to hydrate it. The solvent and the base were removed by distillation and the residue was subjected to column chromatography on silica gel to produce 1.74 g (80% yield) of title product.

(d) 2,6-Dimethyl-5-[2-(N-methyl-N-benzyl)aminoethoxycarbonyl]-4-(2-nitrophenyl)-dihydropyrimidine 3.0 g (31.8 millimole) of acetamidine hydrochloride was added to 40 ml of t-butanol and 3.56 g (31.8 millimole) of t-butoxy potassium was added to the mixture at room temperature. To the mixture a solution of 9.33 g (24.4 millimole) of 2'-nitrobenzylidene-2-(N-methyl-B-benzyl)aminoethyl acetoacetate in 50 ml of t-butanol was added at 0° C. After stirring for 30 minutes, saturated aqueous NaCl solution was added to the mixture and it was extracted with chloroform. The organic phase was dried over anhydrous magnesium sulfate and evaporated to obtain the residue, 9.4 g. 1.08 g of the residue was dissolved in a small amount of chloroform. 10 g of 300 mesh aluminum powder (Wako Junyaku K.K.) was added to the solution and the mixture was homogenized and evaporated.

The aluminum powder was heated at 120° C. for 30 minutes and eluted with chloroform/methanol (5:4). The crude product was purified by aluminum column chromatography (eluant: chloroform) to obtain 0.35 g (37% yield) of title product.

(e) 2,6-Dimethyl-3-ethoxycarbonyl-[2-(N-methyl-N-benzyl)]aminoethoxycarbonyl-4-(2-nitrophenyl)-3,4-dihydropyrimidine 74 mg of 50% Suspension of sodium hydride (1.53 millimole) in oil was suspended in 2 ml of anhydrous tetrahydrofuran. To the suspension a solution of 498 mg (1.18 millimole) of 2,6-dimethyl-5-[2-(N-methyl-N-benzyl)]aminoethoxycarbonyl-4-(2-nitrophenyl)-dihydropyrimidine in 10 ml of anhydrous tetrahydrofuran was added under an argon stream at 0° C. After 5 minutes, the reaction mixture was warmed to room temperature and stirred for further 5 minutes.

To the reaction mixture 137 μl (1.77 millimole) of ethyl chloroformate was added. And saturated aqueous NaCl solution was added to the mixture and it was extracted with chloroform. The organic layer was dried and evaporated under reduced pressure. The residue was dried and evaporated under thin layer chromatography (developer:chloroform:acetone 3:1) to obtain 228 mg (39% yield) of present title product.

EXAMPLE 19

2,6-Dimethyl-3-ethoxycarbonyl-5-cyclopropylmethoxycarbonyl-4-(2-nitrophenyl)-3,4-dihydropyrimidine (a) Cyclopropylmethyl acetoacetate (i) To 13.2 g (179 millimole) of cyclopropyl-carbinol dissolved in 18.1 g (179 millimole) of triethylamine was slowly added 14 ml (179 millimole) of diketene at 0° C. The mixture was stirred at 0° C. for 10 minutes and at room temperature for 30 minutes, diluted with 3% aqueous HCl solution and extracted with chloroform. The organic layer was dried over anhydrous magnesium sulfate and the solvent was evaporated under the reduced pressure to obtain 24 g of cyclopropylmethyl acetoacetate as an oil.

(ii) To 1.0 g (13.9 millimole) of cyclopropylcarbinol was added 1.09 ml (13.9 millimole) of diketene and the mixture was heated at 120° C. for 2 hours to obtain almost quantitatively cyclopropyl methylacetoacetate.

(b) 2-Nitrophenylbenzylidene-cyclopropyl methylacetoacetate 8.2 g (52.6 millimole) of Cyclopropyl methylacetoacetate and 6.6 g (43.8 millimole) of orthonitrobenzaldehyde were dissolved in 55 ml of benzene and 0.44 ml (4.38 millimole) of piperidine was added to the solution and it was dehydrated by refluxing for 15 hrs in a Dean-Stark apparatus. After removing the solvent and base under reduced pressure, the residue was purified on silica gel by chromatography to obtain 6.14 g (49%) of title product.

(c) 2,6-Dimethyl-5-cyclopropylmethoxycarbonyl-4-(2-nitrophenyl)dihydropyrimidine 1.73 g (15.5 millimole) of t-Butoxy potassium was added to 1.46 g (15.5 millimole) of acetamidine hydrochloride in 12 ml of t-butanol. After 5 minutes, a solution of 3.44 g (11.9 millimole) of 2-nitrophenylbenzylidene-cyclopropyl methylacetoacetate in 24 ml of t-butanol was added and stirred for 1.5 hrs at room temperature. The mixture was diluted with saturated aqueous NaCl solution and extracted with CHCl$_3$. The extract was dried over anhydrous magnesium sulfate and evaporated to remove the solvent to obtain 3.18 g of the residue.

The residue was dissolved in 30 ml of benzene 3.48 g (18.33 millimole) of Paratoluenesulfonic acid was added and refluxed for one hour. The solvent was evaporated under reduced pressure and the residue was purified on silica gel by column chromatography (developer:-chloroform/methanol (10:1)) to obtain 880 mg (29% yield) of title produce.

(d) 2,6-Dimethyl-3-ethoxycarbonyl-5-cyclopropylmethoxycarbonyl-4-(2-nitrophenyl)-3,4-dihydropyrimidine 270 mg (0.82 millimole) of 2,6-Dimethyl-5-cyclopropylmethoxycarbonyl-4-(2-nitrophenyl)-dihydropyrimidine in 4 ml of anhydrous tetrahydrofuran was added to 47 mg (0.98 millimole) of sodium hydride as 50% suspension in oil and stirred at room temperature for 5 minutes. Ethyl chloroformate (120 μl), 1.32 millimole) was added and stirred at room temperature for 30 minutes. The reaction solution was diluted with saturated aqueous NaCl solution and extracted with chloroform. The extract was dried over anhydrous magnesium sulfate and evaporated under reduced pressure to remove the solvent. The residue was purified on silica gel by thin layer chromatography (developer:-chloroform/acetone 10:1, eluant : chloroform/methanol 4:1) to obtain 196 mg (yield 60%) of title compound.

EXAMPLE 20

5-Cyclopropylmethoxycarbonyl-2,6-dimethyl-3-n-heptyloxycarbonyl-4-(3-nitrophenyl)-3,4-dihydropyrimidine 5-Cyclopropylmethoxycarbonyl-2,6-dimethyl-4-(3-nitrophenyl)-3,4-dihydropyrimidine (0.50 g, 1.52 millimole) prepared in Example 19 in 10 ml of anhydrous dioxane was added at room temperature to a suspension of 1 g (20.8 millimole) of sodium hydride (as 50% suspension in oil) in 5 ml of anhydrous dioxane and stirred for 30 minutes. 0.30 g (1.68 millimole) of n-Heptyl chloroformate was added dropwise, stirred at room temperature for 30 minutes and chilled to 0° C. Water was added and extracted with ether. The extract was washed with water, dried over anhydrous magnesium sulfate and evaporated to obtain the crude product (0.68 g). It was purified on silica gel be column chromatography (eluant:benzene) to obtain 400 mg (56% yield) of title compound.

Yield (%) and physicochemical data of products obtained in Examples 18-20 are shown in the following Table 3.

EXAMPLES 21-37

By the method of Example 18, the following products were obtained from the appropriate starting materials. Yield (%) and physicochemical data of the products are also shown in Table 3.

TABLE 3

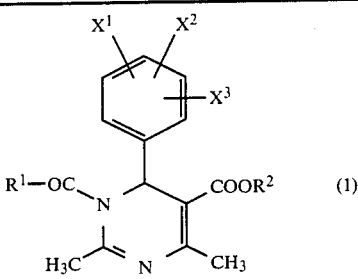

(1)

| Ex. No. | Compound | Yield (%) | Properties (Recrystallization solvents) | IR spectrum ($cm^{-1}$) | NMR spectrum ($CDCl_3$, δ ppm) 270 MHz | High resolution mass spectrum |
|---|---|---|---|---|---|---|
| 18 | $R^1$=ethoxy $R^2$=methylbenzylaminoethyl $X^1$=2-nitro $X^2=X^3$=H | 39 | m.p. 83-84° (ethyl acetate. hexane) | 1730, 1710 (film) | 1.32(3H,t,J=7Hz), 2.12(3H,s), 2.34(3H,s), 2.46(3H,s), 2.68 (2H, m), 3.42(1H,d,J=14Hz), 3.48(1H,d, J=14Hz), 4.26(4H,m), 6.87(1H, brs), 7.19-7.78(4H,m) | Calculated for $C_{26}H_{30}N_4O_6$: 494.2166 Found: 494.2198 |
| 19 | $R^1$=ethoxy $R^2$=cyclopropylmethyl $X^1$=2-nitro $X^2=X^3$=H | 60 | m.p. 97-97.5° (ether. hexane) | 1730, 1700 (chloroform) | 0.18(2H,m), 1.10(1H, m), 1.33(3H,t,J=7Hz), 2.36(3H,s) 2.47(3H,brs), 3.93(2H,m), 4.26(2H,m), 6.90(1H,s), 7.36-7.83(4H,m) | Calculated for $C_{20}H_{23}N_3O_6$: 401.1588 Found: 401.1590 |
| 20 | $R^1$=n-heptyloxy $R^2$=cyclopropylmethyl $X^1$=3-nitro $X^2=X^3$=H | 55 | oil | 1720, 1710 (chloroform) | 0.20-0.55(4H,m), 0.88(3H,t, J=7Hz), 1.05-1.15(1H,m), 1.22-1.35(8H,m), 1.70-1.80(2H,m), 2.43(3H,s), 2.47(3H,s), 3.90-4.01(2H,m), 4.27(2H,t,J=7Hz), 6.29(1H,s), 7.28-8.17(4H,m) | Calculated for $C_{25}H_{33}N_3O_6$: 471.5560 Found: 471.5541 |
| 21 | $R^1$=methoxy $F^2$=methylbenzylaminoethyl $X^1$=2-nitro $X^2=X_3$=H | 40 | oil | 1740, 1710 (chloroform) | 2.08(3H,brs), 2.34(3H,s), 2.46(3H,brs), 2.69(2H,m), 3.42(1H,d,J=1 3.47(1H,d, J=11Hz), 3.77(3H,s), 4.26(2H,m), 6.81(1H,s), 71.8-7.76(4H.m) | Calculated for $C_{25}H_{28}N_4O_6$: 480.2006 Found: : 480.1958 |
| 22 | $R^1$=2-ethylhexyl $R^2$=methylbenzylaminoethyl X=2-nitro $X^2=X^3$=H | 36 | oil | 1720, 1700 (chloroform) | 0.86(6H,m), 1.20-1.45(9H,m), 2.12(3H,s), 2.33(3H,s), 2.45(3H,s), 2.70(2H,brt), 3.45(2H,m), 4.00-4.35(4H,m), 6.84(1H,s), 7.18-7.75(4H,m) | Calculated for $C_{32}H_{42}N_4O_6$: 578.3102 Found: 578.3072 |
| 23 | $R^1$=ethoxy $R^2$=ethylethoxycarbonylaminoethyl $X^1$=2-nitro $X^2=X^3$=H | 37 | oil | 1730, 1700 (chloroform) | 1.20(3H,t,J=7Hz), 1.32(3H,t, J=7Hz), 2.33(3H,s), 2.43(3H,s), 2.74(3H,s), 3.35-3.68(2H,m), 3.88-4.43(6H,m), 6.88(1H,brs), 7.20-7.80(4H,m) | Calculated for $C_{22}H_{28}N_4O_6$: 476.1907 Found: 476.1943 |
| 24 | $R^1$= ethoxy $R^2$=2-methoxyethyl $X^1$=2-nitro $X^2=X^3$=H | 64 | m.p. 85.5-86.5° | 1720, 1705 (chloroform) | 1.33(3H,t,J=7Hz), 2.35(3H,s), 2.46(3H,s), 3.27(3H,s), 35Hz), 4.19(2H,t, J=5Hz), 4.26(2H,q,J=7Hz), 6.89(1H,s), 7.3-8.1(4H,m) | Calculated for $C_{19}H_{23}N_3O_7$: 405.4095 Found: 405.4099 |
| 25 | $R^1$=2-methylpropyloxy $R^2$=2-methoxyethyl $X^1$=2-nitro $X^2=X^3$ =H | 76 | oil | 1730, 1720 (chloroform) | 0.92(6H,d,J=6.6Hz), 1.85-2.15 (1H,m),2.35(3H,s), 2.45(3H,s), 3.28(3H,s), 3.56(2H,t,J=4.5Hz), 3.94(1H,d,J=7Hz), 3.98(1H,d, J=7Hz), 4.22(2H,t,J=4.5Hz), 6.85(1H,s), 7.4-7.8(4H,m) | Calculated for $C_{21}H_{27}N_3O_7$: 433.4634 Found: 433.4633 |
| 26 | $R^1$=2-ethylhexyloxy $R^2$=2-phenoxyethyl $X^1$=2-nitro $X^2=X^3$=H | 22 | oil | 1730, 1710 (chloroform) | 0.86(6H,brt,J=7Hz), 1.20-1.75 (9H,m), 2.33(3H,s), 2.47(3H,brs), 4.00-4.20(4H,m), 4.38-4.55(2H,m), 6.72-7.65(9H,m), 6.88(1H,brs) | Calculated for $C_{30}H_{37}N_3O_7$: 551.2632 Found: 551.2638 |
| 27 | $R^1$=2-methoxyethyloxy $R^2$=cyclopropylmethyl $X^1$=2-nitro $X^2=X^3$=H | 78 | oil | 1730, 1700 (chloroform) | 0.03-0.63(4H,m), 0.90-1.05(1H,m), 2.30(3H,s), 2.40(3H,d,J=1Hz), 3.30(3H,s), 3.58(2H,m), 3.75(2H, m), 4.21(2H,m), 6.02(1H,brs), 7.20-7.80(4H,m) | Calculated for $C_{21}H_{25}N_3O_7$: 431.1693 Found: 431.1725 |
| 28 | $R^1$=n-nonyloxy $R^2$=cyclopropylmethyl $X^1$=2-nitro $X^2=X^3$= H | 16 | oil | 1720, 1700 (chloroform) | 0.07-0.18(2H,m), 0.45-0.50(2H,m), 0.86(3H,t,J=6.6Hz), 1.10-1.60 (1H,m), 1.20-1.40(12H,m), 1.69 (2H,m), 2.39(3H,s), 2.46(3H,s), 3.85-4.00(2H,m), 4.10-4.26(2H,m), 6.99(1H,s), 7.40-7.78(4H,m) | Calculated for $C_{27}H_{37}N_3O_6$: 499.6099 Found: 499.6129 |

TABLE 3-continued

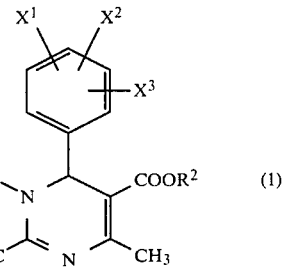

(1)

| Ex. No. | Compound | Yield (%) | Properties (Recrystallization solvents) | IR spectrum (cm$^{-1}$) | NMR spectrum (CDCl$_3$, δ ppm) 270 MHz | High resolution mass spectrum |
|---|---|---|---|---|---|---|
| 29 | R$^1$=n-octyloxy<br>R$^2$=cyclopropylmethyl<br>X$^1$=2-bromo<br>X$^2$=X$^3$=H | 86 | oil | 1720, 1700 (chloroform) | 0.10–0.70(4H,m), 0.88(3H,t, J=7Hz), 1.00–1.30(1H,m), 1.10–1.90(12H,m), 2.42(6H,s), 3.93(2H,d,J=7Hz), 4.05–4.35(2H, m), 6.55(1H,s), 7.00–7.60(4H,m) | Calculated for C$_{26}$H$_{35}$BrN$_2$O$_4$: 519.4914<br>Found: 519.4836 |
| 30 | R$^1$=2-ethylhexyloxy<br>R$^2$=cyclopropylmethyl<br>X$^1$=2-chloro<br>X$^3$=X$^3$=H | 30 | oil | 1720, 1705 (chloroform) | 0.15–0.28(2H,m), 0.42–0.55(2H,m), 0.80–1.00(6H,m), 1.00–1.18(1H,m), 1.18–1.78(9H,m), 2.42(3H,s), 2.43(3H,s), 3.91(2H,d,J=7Hz), 4.10–4.25(2H,m), 6.62(1H,s), 7.10–7.42(4H,m) | Calculated for C$_{26}$H$_{35}$ClN$_2$O$_4$: 475.0304<br>Found: 475.0310 |
| 31 | R$^1$=cyclopropyl-methyloxy<br>R$^2$=cyclopropylmethyl<br>X$^1$=3-nitro<br>X$^2$=X$^3$=H | 35 | oil | 1720, 1710 (chloroform) | 0.15–0.78(8H,m), 1.00–1.35(2H,m), 2.44(3H,s), 2.48(3H,s), 3.90–4.15(2H,m), 4.12(2H,d,J=7.5Hz), 6.30(1H,s), 7.48(1H,t,J=8Hz), 7.62(1H,d,J=8Hz), 8.15(1H,d J=8Hz), 8.20(1H,s) | Calculated for C$_{22}$H$_{25}$N$_3$O$_6$: 427.4593<br>Found: 427.4600 |
| 32 | R$^1$=5-phenylpentyloxy<br>R$^2$=cyclopropylmethyl<br>X$^1$=3-nitro<br>X$^2$=X$^3$=H | 47 | oil | 1720, 1700 (chloroform) | 0.15–0.30(2H,m), 0.45–0.65(2H,m), 1.05–1.20(1H,m), 1.40–1.90(6H,m), 2.42(3H,s), 2.50(3H,brs), 2.65(2H,t,J=8Hz), 4.00(2H,m), 4.30(2H,t,J=8Hz), 6.30(1H,s), 7.13–7.40(5H,m), 7.43–8.24(4H,m) | Calculated for C$_{29}$H$_{33}$N$_3$O$_6$: 519.6006<br>Found: 519.6016 |
| 33 | R$^1$=n-heptyloxy<br>R$^2$=cyclopropylmethyl<br>X$^1$=2-nitro<br>X$^2$=X$^3$=H | 56 | oil | 1720, 1700 (chloroform) | 0.10–0.25(2H,m), 0.40–0.55(2H,m), 0.80–0.95(3H,m), 1.05–1.20(1H,m), 1.20–1.75(10H,m), 2.35(3H,s), 2.46(3H,brs), 3.85–4.00(2H,m), 4.08–4.30(2H,m), 6.90(1H,s), 7.35–7.80(4H,m) | Calculated for C$_{25}$H$_{33}$N$_3$O$_6$: 471.5560<br>Found: 471.5581 |
| 34 | R$^1$=2-ethylhexyloxy<br>R$^2$=cyclopropylmethyl<br>X$^1$=2-nitro<br>X$^2$=X$^3$=H | 83 | oil | 1725, 1700 (chloroform) | 0.10–0.25(2H,m), 0.35–0.55(2H,m), 0.70–1.00(6H,m), 1.00–1.25(1H,m), 1.10–1.80(9H,m), 2.34(3H,s), 2.46(3H,brs), 3.80–4.05(2H,m), 4.05–4.30(2H,m), 6.90(1H,s), 7.35–7.85(4H,m) | Calculated for C$_{26}$H$_{35}$N$_3$O$_6$: 485.5829<br>Found: 485.5835 |
| 35 | R$^1$=ethoxy<br>R$^2$=diethylaminoethyl<br>X$^1$=2-nitro<br>X$^2$=X$^3$=H | 75 | m.p. 74–75° (chloroform, hexane) | 1730, 1710 | 0.96(6H,t,J=7Hz), 1.33(3H,t, J=7Hz), 2.34(3H,s), 2.45(3H,s), 2.45–2.55(6H,m), 4.10–4.38(4H,m), 6.85(1H,s), 7.38–7.80(4H,m) | Calculated for C$_{22}$H$_{30}$N$_4$O$_6$: 446.2162<br>Found: 446.2117 |
| 36 | R$^2$=5-phenylpentyloxy<br>R$^2$=cyclopropylmethyl<br>X$^1$=2-nitro<br>X$^2$=X$^3$=H | 21 | oil | 1730, 1705 | 0.15–0.25(2H,m), 0.40–0.55(2H,m), 1.05–1.15(1H,m), 1.25–1.80(6H,m), 2.33(3H,s), 2.46(3H,brs), 2.61(2H,t,J=8Hz), 3.82–3.98 (2H,m), 4.05–4.30(2H,m), 6.89(1H,s), 7.12–7.80(9H,m) | Calculated for C$_{29}$H$_{33}$N$_3$O$_6$: 519.2367<br>Found: 519.2344 |
| 37 | R$^1$=4-phenylbutyloxy<br>R$^2$=cyclopropylmethyl<br>X$^1$=2-nitro<br>X$^2$=X$^3$=H | 38 | oil | 1730, 1700 | 0.13–0.20(2H,m), 0.40–0.47(2H,m), 1.03–1.14(1H,m), 1.60–1.78(4H,m), 2.34(3H,s), 2.46(3H,s), 2.64(2H,t,J=7Hz), 3.84–3.98 (2H,m), 4.11–4.31(2H,m), 6.90(1H,s), 7.14–7.77(4H,m) | Calculated for C$_{28}$H$_{31}$N$_3$O$_6$: 505.2213<br>Found: 505.2216 |

EXAMPLE 38

5-(n-Butyloxycarbonyl)-4-(2-chlorophenyl)-3-(2-ethylhexyloxycarbonyl)-2,6-dimethyl-3,4-dihydropyrimidine A solution of 1.4 g of 5-(n-butyloxycarbonyl)-4-(2-chlorophenyl)-2,6-dimethyl-dihydropyrimidine in 10 ml of tetrahydrofuran was added at room temperature to a suspension of 1 g of sodium hydride (as 50% suspension) in 5 ml of tetrahydrofuran. After 20 minutes, a solution of 1 g of 2-ethylhexyl chloroformate in 5 ml of tetrahydrofuran was added dropwise and after 30 minutes the reaction solution was diluted with ice water and extracted three times with ether. The organic layer was washed twice with water and dried over anhydrous magnesium sulfate and evaporated to remove the solvent to obtain 2 g of the residue. It was purified on 50 g of silica gel by column chromatography and eluted with 0.5% methanol/chloroform to obtain 1.47 g (71% yiled) of title compound.

EXAMPLE 39

3-(2-Heptyloxycarbonyl)-2,6-dimethyl-5-(3-methyl-2-butenyloxycarbonyl)-4-(3,4,5-trimethoxyphenyl)-3,4-dihydropyrimidine 0.5 ml of Triethylamine was added to a solution of 200 mg of 2,6-dimethyl-5-(3-methyl-2-butenyloxycarbonyl)-4-(3,4,5-trimethoxyphenyl)-dihydropyrimidine in 5 ml of tetrahydrofuran (THF) and 2-heptyl chloroformate dissolved in 6 ml of THF was added dropwise. The 2-heptyl chloroformate was prepared by adding 0.25 ml of N,N-diethylaniline dissolved in 2 ml of THF to a solution of 0.15 g of 2-heptyn-1-ol and 0.1 mg of trichloromethyl chloroformate in 4 ml of THF in a separate reaction vessel. After stirring at room temperature for 1 hr, the reaction mixture was concentrated under reduced pressure. The residue was purified on silica gel by column chromatography (silica gel 20 g, eluant:benzene/ethyl acetate 9:1) to obtain 187 mg (69% yield) of title product.

EXAMPLE 40

5-Isopropyloxycarbonyl-2,6-dimethyl-4-(2-nitrophenyl)-3-(4-n-propyloxycarbonylphenyloxycarbonyl)-3,4-dihydropyrimidine A solution of 250 mg (1.35 millimole) of n-propyl-p-hydroxybenzoate in 7 ml of THF was added to a solution of 0.12 ml (1.00 millimole) of trichloromethyl chloroformate in 2 ml of THF and then a solution of 0.25 ml (1.57 millimole) of N,N-diethylaniline in 6 ml of THF was added dropwise. The reaction mixture was stirred for 1.5 hrs at room temperature. Independently, 0.30 g (6.25 millimole) of sodium hydride washed with hexane was suspended in 5 ml of THF and a solution of 200 mg (0.63 millimole) of 5-isopropyloxycarbonyl-2,6-dimethyl-4-(2-nitrophenyl)-dihydropyrimidine in 5 ml os THF was added dropwise and stirred for 40 minutes at room temperature. And to this mixture the above reaction mixture was added and stirred for 30 minutes. Ice water was added and the mixture was extracted three times with ether. The organic layer was washed twice with water, dried over magnesium sulfate (dehydrating agent) and concentrated under reduced pressure. The residue was purified on silica gel by column chromatography (silica gel 30 g, eluant:benzene/ethyl acetate 9:1) to obtain 117 mg (35% yield) of tilte compound.

Physicochemical data of products obtained in Examples 38-40 are shown in Table 4.

By the methods of Examples 38-40, products of Examples 41-63 were obtained. Physicochemical data of the products are also shown in Table 4.

TABLE 4

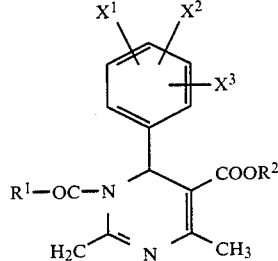

(1)

| Ex. No. | Compound | Yield (%) | Properties | IR spectrum (cm$^{-1}$) | NMR spectrum (CDCl$_3$, δ ppm, 270 MHz) | High resolution mass spectrum |
|---|---|---|---|---|---|---|
| 38 | $X^1$=2-chloro $X^2$=$X^3$=H $R^1$=2-ethylhexyloxy $R^2$=n-butyl | 71 | colorless oil | (chloroform) 1725, 1710 | 0.83–0.92(9H,m), 1.20–1.40(10H, m), 1.53–1.71(3H,m), 2.40(3H,s), 2.43(3H,s), 4.06–4.23(4H,m), 6.60(1H,s), 7.13–7.36(4H,m) | Calculated for C$_{26}$H$_{37}$ClN$_2$O$_4$: 477.0462 Found: 477.0492 |
| 39 | $X^1$=$X^2$=$X^3$=methoxy $R^1$=2-heptynyloxy $R^3$=3-methyl-2-butenyl | 69 | colorless oil | (chloroform) 2240, 1730, 1710 | 0.90(3H,t,J=7Hz), 1.35–1.55 4H,m), 1.65(3H,s), 1.73(3H,s), 2.22(2H,t,J=7Hz), 2.41(3H,s), 2.42(3H,s), 3.81(9H,brs), 4.55–4.70(2H,m), 4.84(2H,brs), 5.32(1H,t,J=7Hz), 6.13(1H,s), 6.53(2H,s) | Calculated for C$_{29}$H$_{38}$N$_2$O$_7$: 526.6328 Found: 526.6301 |
| 40 | $X^1$=2-nitro $X^2$=$X^3$=H $R^1$=4-n-propyloxy-carbonylphenyloxy $R^2$=isopropyl | 35 | colorless oil | (chloroform) 1745, 1710 | 1.03(3H,t,J=7Hz), 1.08(3H,d, J=6Hz), 1.29(3H,d,J=6Hz), 1.75–1.83(2H,m), 2.41(3H,s), 2.51 (3H,s), 4.29(2H,t,J=7Hz), 5.01–5.10(1H,m), 7.07(1H,s), 7.26 (2H,d,J=9Hz), 7.35–7.81(4H,m), 8.09(2H,d,J=9Hz) | Calculated for C$_{27}$H$_{29}$N$_3$O$_8$: 523.5455 Found: 523.5476 |
| 41 | $X^1$=2-nitro $X^2$=$X^3$=H $R^1$=benzyloxy $R^2$=isopropyl | 79 | yellow oil | (chloroform) 1730, 1700 | 1.06(3H,d,J=6Hz), 1.28(3H,d, J=6Hz), 2.27(3H,s), 2.43(3H,s), 5.00–5.26(1H,m), 5.10(1H,d, J=13Hz), 5.28(1H,d,J=13Hz), 6.87(1H,s), 7.36–7.79(9H,m) | Calculated for C$_{24}$H$_{25}$N$_3$O$_6$: 451.4816 Found: 451.4820 |
| 42 | $X^1$=2-nitro $X^2$=$X^3$=H $R^1$=n-hexyloxy $R^2$=isopropyl | 59 | yellow oil | (chloroform) 1740, 1710 | 0.88(3H,t,J=7Hz), 1.06(3H,d, J=6Hz), 1.27–1.30(3H,d,J=6Hz & 8H,m), 2.32(3H,s), 2.46(3H,s), 4.14–4.23(2H,m), 5.01–5.05(1H, m), 6.87(1H,s), 7.39–7.78(4H,m) | Calculated for C$_{23}$H$_{31}$N$_3$O$_6$: 445.5179 Found: 445.5199 |
| 43 | $X^1$=2-nitro | 96 | yellow | (chloroform) | 0.75–1.05(9H,m), 1.15–1.85 | Calculated for |

TABLE 4-continued

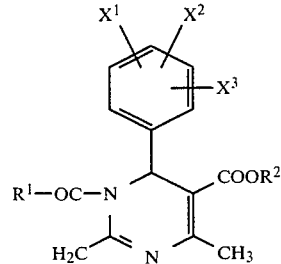

(1)

| Ex. No. | Compound | Yield (%) | Properties | IR spectrum (cm$^{-1}$) | NMR spectrum (CDCl$_3$, δ ppm, 270 MHz) | High resolution mass spectrum |
|---|---|---|---|---|---|---|
| | $X^2=X^3=H$<br>$R^1=$2-ethylhexyloxy<br>$R^2=$n-propyl | | oil | 1720, 1700 | (11H,m), 2.33(3H,s), 2.47(3H,s), 3.95–4.30(4H,m), 6.88(1H,s), 7.30–7.90(4H,m) | C$_{25}$H$_{35}$N$_3$O$_6$: 473.5718<br>Found: 473.5710 |
| 44 | $X^1=$2-nitro<br>$X^2=X^3=H$<br>$R^1=$cis-3-hexenyloxy<br>$R^2=$n-propyl | 56 | yellow oil | (chloroform) 1720, 1700 | 0.80(3H,t,J=7Hz), 0.93(3H,t, J=7Hz), 1.55–1.75(2H,m), 1.90–2.15(2H,m), 2.33(3H,s), 2.35–2.55(5H,m), 4.00–4.35(4H,m, 5.20–5.35(1H,m), 5.40–5.60(1H,m), 6.86(1H,s), 7.30–7.85(4H,m) | Calculated for C$_{23}$H$_{29}$N$_3$O$_6$: 443.5021<br>Found: 443.5040 |
| 45 | $X^1=$2-chloro<br>$X^2=X^3=H$<br>$R^1=$cyclopropylmethyl<br>$R^2=$n-butyl | 65 | yellow oil | (chloroform) 1725, 1715 | 0.29–0.34(2H,m), 0.57–0.61(2H,m), 0.86(3H,t,J=7Hz), 1.19–1.29 (3H,m), 1.53–1.64(2H,m), 2.44(6H,brs), 4.03–4.12(4H,m), 6.62(1H,s), 7.16–7.35(4H,m) | Calculated for C$_{22}$H$_{27}$ClN$_2$O$_4$: 418.9226<br>Found: 418.9245 |
| 46 | $X^1=$2-nitro<br>$X^2=X^3=H$<br>$R^1=$ethoxy<br>$R^2=$isobutyl | 44 | yellow oil | (chloroform) 1730, 1710 | 0.76(3H,d,J=7Hz), 0.83(3H,d, J=7Hz), 1.34(3H,t,J=7Hz), 1.89–1.99(1H,m), 2.33(3H,s), 2.48 (3H,s), 3.85–3.95(2H,m), 4.15–4.38(2H,m), 6.88(1H,s), 7.37–7.77(4H,m) | Calculated for C$_{20}$H$_{25}$N$_3$O$_6$: 403.4370<br>Found: 403.4355 |
| 47 | $X^1=$2-nitro<br>$X^2=X^3=H$<br>$R^1=$heptyloxy<br>$R^2=$isobutyl | 68 | colorless oil | (chloroform) 1725, 1700 | 0.77(3H,d,J=7Hz), 0.83(3H,d, J=7Hz), 0.88(3H,t,J=7Hz), 1.25–1.32(8H,m), 1.65–1.72(2H,m), 2.47(3H,s), 3.90(2H,d,J=6Hz), 4.08–4.30(2H,m), 6.87(1H,s), 7.35–7.76(4H,m) | Calculated for C$_{25}$H$_{35}$N$_3$O$_6$: 473.5718<br>Found: 473.5735 |
| 48 | $X^1=$2-nitro<br>$X^2=X^3=H$<br>$R^1=$3-phenylpropyloxy<br>$R^2=$isobutyl | 44 | colorless oil | (chloroform) 1730, 1710 | 0.76(3H,d,J=7Hz), 0.82(3H,d J=7Hz), 1.85–2.10(3H,m), 2.32(3H,s), 2.48(3H,s), 2.68 (2H,t,J=8Hz), 3.85–3.95(2H,m), 4.13–4.33(2H,m), 6.87(1H,s), 7.15–7.74(9H,m) | Calculated for C$_{27}$H$_{31}$N$_3$O$_6$: 493.5625<br>Found: 493.5651 |
| 49 | $X^1=$2-nitro<br>$X^2=X^3=H$<br>$R^1=$ethoxy<br>$R^2=$sec-butyl | 99 | colorless oil | (chloroform) 1730, 1700 | 0.48, 0.90(each 3H,t,J=7Hz), 1.02, 1.26(each 3H,d,J=6Hz), 1.33(3H×2,t,J=7Hz), 1.20–1.80 2H×2,m), 4.10–4.45(2H×2,m), 4.75–5.00(1H×2,m), 6.86, 6.89 (each 1H,s), 7.30–7.90(4H×2,m) | Calculated for C$_{20}$H$_{25}$N$_3$O$_6$: 403.4370<br>Found: 403.4341 |
| 50 | $X^1=$2-nitro<br>$X^2=X^3=H$<br>$R^1=$5-phenylpentyloxy<br>$R^2=$sec-butyl | 49 | yellow oil | (chloroform) 1725, 1705 | 0.48, 0.87(each 3H,t,J=7Hz), 1.02, 1.26(each 3H,d,J=6Hz), 1.30–1.85(8H×2,m), 2.28, 2.49 (each 3H,s), 2.30, 3.47(each 3H,s), 2.62(2H×2,t,J=8Hz), 4.05–4.35(2H×2,m), 4.75–5.00 (1H×2,m), 6.86, 6.88(each 1H×2,s), 7.05–7.90(9H×2,m) | Calculated for C$_{29}$H$_{35}$N$_3$O$_6$: 521.6164<br>Found: 521.6190 |
| 51 | $X^1=$2-nitro<br>$X^2=X^3=H$<br>$R^1=$ethoxy<br>$R^2=$3,3-dimethylbutyl | 73 | m.p. 106–107° (ether. hexane) | (film) 1735, 1710 | 0.86(9H,s), 1.33(3H,t,J=7Hz), 1.57(2H,m), 2.34(3H,s), 2.46 (3H,brs), 4.18(2H,m), 4.30(2H,m), 6.85(1H,s), 7.35–7.78(4H,m) | Calculated for C$_{22}$H$_{29}$N$_3$O$_6$: 431.2054<br>Found: 431.2043 |
| 52 | $X^1=$4-methylthio<br>$X^2=X^3=H$<br>$R^1=$ethoxy<br>$R^2=$2-ethylbutyl | 79 | colorless oil | (chloroform) 1710 | 0.78–0.85(6H,m), 1.24–1.32(4H,m), 1.38(3H,t,J=7Hz), 1.45(1H,m), 4.00–4.04(2H,m), 4.29–4.33(2H,m), 6.16(1H,s), 7.13–7.29(4H,m) | Calculated for C$_{22}$H$_{32}$N$_2$O$_4$S: 420.5731<br>Found: 420.5760 |
| 53 | $X^1=$4-methylthio<br>$X^2=X^3=H$<br>$R^1=$n-heptyloxy<br>$R^2=$2-ethylbutyl | 77 | colorless oil | (chloroform) 1720, 1700 | 0.77–1.18(9H,m), 1.18–1.75 15H,m), 2.36(3H,s), 2.44(6H,s), 3.99–4.04(2H,m), 4.22–4.27(2H,m), 6.15(1H,s), 7.12–7.21(4H,m) | Calculated for C$_{28}$H$_{42}$N$_2$O$_4$S: 502.2862<br>Found: 502.2857 |
| 54 | $X^1=$2-bromo<br>$X^2=X^3=H$<br>$R^1=$ethoxy<br>$R^2=$n-pentyl | 42 | colorless oil | (chloroform) 1730, 1710 | 0.84(3H,t,J=7Hz), 1.10–1.75(6H, m), 1.37(3H,t,J=7Hz), 2.41(3H,s), 2.43(3H,s), 4.10(2H,m), 4.32(2H, m), 6.53(1H,s), 7.08–7.60(4H,m) | Calculated for C$_{21}$H$_{27}$BrN$_2$O$_4$: 451.3625<br>Found: 451.3654 |
| 55 | $X^1=$3-trifluoromethyl<br>$X^2=X^3=H$<br>$R^1=$n-heptyloxy<br>$R^2=$n-pentyl | 56 | colorless oil | (chloroform) 1720, 1705 | 0.80–0.95(6H,m), 1.15–1.80 (16H,m), 2.39(3H,s), 2.45(3H,s), 4.00–4.20(2H,m), 4.26(2H,t,J=7Hz), 6.21(1H,s), | Calculated for C$_{27}$H$_{37}$F$_3$N$_2$O$_4$: 510.5996<br>Found: 510.6007 |

TABLE 4-continued

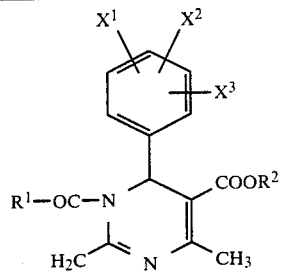

(1)

| Ex. No. | Compound | Yield (%) | Properties | IR spectrum (cm$^{-1}$) | NMR spectrum (CDCl$_3$, δ ppm, 270 MHz) | High resolution mass spectrum |
|---|---|---|---|---|---|---|
| 56 | $X^1$=2-nitro<br>$X^2$=$X^3$=H<br>$R^1$=ethoxy<br>$R^2$=heptyl | 82 | yellow crystals m.p. 71–73° (benzene. hexane) | (chloroform) 1720, 1695 | 7.40–7.60(4H,m)<br>0.85(3H,t,J=7Hz), 1.00–1.80<br>(10H,m), 1.33(3H,t,J=7Hz),<br>2.34(3H,s), 2.47(3H,s),<br>4.05–4.40(4H,m), 6.86(1H,s),<br>7.30–7.85(4H,m) | Calculated for $C_{23}H_{31}N_3O_6$: 445.5179<br>Found: 445.5149 |
| 57 | $X^1$=2-nitro<br>$X^2$=$X^3$=H<br>$R^1$=n-heptyloxy<br>$R^2$=n-heptyl | 79 | colorless oil | (chloroform) 1730, 1710 | 0.75–1.00(6H,m), 1.05–1.85<br>(20H,m), 2.33(3H,s), 2.46<br>(3H,brs), 4.05–4.35(4H,m),<br>6.86(1H,s), 7.30–7.90(4H,m) | Calculated for $C_{28}H_{41}N_3O_6$: 515.6526<br>Found: 515.6554 |
| 58 | $X^1$=3-cyano<br>$X^2$=$X^3$=H<br>$R^1$=ethoxy<br>$R^2$=2-cyclopentylethyl | 83 | colorless oil | (chloroform) 2210, 1720, 1700 | 0.90–1.80(11H,m), 1.39(3H,t,<br>J=7Hz), 2.37(3H,s), 2.46(3H,s),<br>4.00–4.25(2H,m), 4.25–4.45(2H,m),<br>6.20(1H,s), 7.30–7.70(4H,m) | Calculated for $C_{24}H_{29}N_3O_4$: 423.5144<br>Found: 423.5170 |
| 59 | $X^1$=2-nitro<br>$X^2$=$X^3$=H<br>$R^1$=geranyloxy<br>$R^2$=n-propyl | 32 | colorless oil | (chloroform) 1725, 1705 | 0.79(3H,t,J=7Hz), 1.45–1.85<br>(2H,m), 1.59(3H,s), 1.66(3H,s),<br>1.73(3H,s), 1.90–2.25(4H,m),<br>2.33(3H,s), 2.46(3H,s), 4.06<br>(2H,t,J=7Hz), 4.55–4.85(2H,m),<br>5.00–5.15(1H,m), 5.30–5.45(1H,m),<br>6.86(1H,s), 7.35–7.85(4H,m) | Calculated for $C_{27}H_{35}N_3O_6$: 497.5941<br>Found: 497.5952 |
| 60 | $X^1$=2-nitro<br>$X^2$=$X^3$=H<br>$R^1$=2-cyclopentyl-ethyloxy<br>$R^2$=isopropyl | 42 | colorless oil | (chloroform) 1730, 1700 | 1.07(3H,d,J=6Hz), 1.29(3H,d,<br>J=6Hz), 1.45–1.90(11H,m),<br>2.32(3H,s), 2.46(3H,brs),<br>4.10–4.35(2H.m), 5.05(1H,m),<br>6.86(1H,s), 7.35–7.82(4H,m) | Calculated for $C_{24}H_{31}N_3O_6$: 457.5290<br>Found: 457.5299 |
| 61 | $X^1$=2-nitro<br>$X^2$=$X^3$=H<br>$R^1$=2-(3,4-dimethoxy-phenyl)ethoxy<br>$R^2$=isopropyl | 55 | colorless oil | (chloroform) 1725, 1700 | 1.06(3H,d,J=6Hz), 1.29(3H,d,<br>J=6Hz), 2.23(3H,s), 2.45(3H,s),<br>2.99(2H,t,J=7Hz), 3.84(3H×2,s×2),<br>4.25–4.55(2H,m), 4.90–5.15<br>(1H,m), 6.65–6.85(3H,m),<br>6.84(1H,s), 7.30–7.90(4H,m) | Calculated for $C_{27}H_{31}N_3O_8$: 525.5613<br>Found: 525.5634 |
| 62 | $X^1$=2-nitro<br>$X^2$=$X^3$=H<br>$R^1$=2-nitrobenzyloxy<br>$R^2$=isopropyl | 12 | colorless oil | (chloroform) 1740, 1705 | 1.07(3H,d,J=6Hz), 1.29(3H,d,<br>J=6Hz), 2.31(3H,s), 2.46(3H,brs),<br>5.04(1H,m), 5.52(1H,d,J=14Hz),<br>5.70(1H,d,J=14Hz), 6.92(1H,s),<br>7.35–7.80(3H,m), 8.14(1H,d,J=8Hz) | Calculated for $C_{24}H_{24}N_4O_8$: 496.4792<br>Found: 496.4766 |
| 63 | $X^1$=2-nitro<br>$X^2$=$X^3$=H<br>$R^1$=4-nitrophenyloxy<br>$R^2$=n-propyl | 63 | m.p. 136–138° (benzene. hexane) | (chloroform) 1750, 1705 | 0.81(3H,t,J=7Hz), 1.50–1.80<br>(2H,m), 2.42(3H,s), 2.52(3H,s),<br>4.10(2H,t,J=7Hz), 7.06(1H,s),<br>7.40(2H,brd,J=9Hz), 7.35–7.85<br>(4H,m), 8.29(2H,brd,J=9Hz) | Calculated for $C_{23}H_{22}N_4O_8$: 482.4523<br>Found: 482.4550 |

EXAMPLE 64

The pharmacological effect (ED$_{30}$) of the compounds of the present invention with respect to the resistance of the vessels of vertebral artery in anesthetized dogs was tested by the following procedure.

Test method

Male and female dogs (7–14 kg in weight) were induction-anesthetized with thiopental sodium (35 mg/kg, intraperitoneal), anesthetized with urethane (400 mg/kg, intravenous) and chloralose (60 mg/kg, intravenous) and kept under artificial respiration during the test. The first and second ribs were cut open to expose the left vertebral artery. A probe was attached to the origin of the artery and the blood flow was measured with an electromagnetic rheometer (Model MF-27, product of Nihon Koden K.K.).

At the same time, continuous measurement of the following parameters was made: systemic blood pressure (average pressure) at the right femoral artery, the ECG in the second induction period, the heart beat with a tachometer driven by the R wave, and the blood vessel resistance determined by loading a multilication/division unit (EO-601 G, product of Nihon Koden K.K.) with the average values of blood pressure and blood flow in the vertebral artery. All of these parameters were recorded simultaneously on a polygraph (RM-600, product of Nihon Koden, K.K.).

All the test compounds were injected through a cannula inserted into the femoral vein.

The ED₃₀ (μg/kg) values obtained by intravenous injection are listed in Table 5, wherein the Compound Numbers are keyed to the Example Numbers.

TABLE 5

| Compound No. | $ED_{30}$ (μg/kg) |
|---|---|
| 1 | 9.2 |
| 2 | 12.0 |
| 3 | 8.6 |
| 4 | 9.0 |
| 5 | 13.0 |
| 6 | 8.5 |
| 7 | 5.9 |
| 9 | 12.0 |
| 10 | 16.0 |
| 12 | 3.2 |
| 13 | 3.0 |
| 17 | 15.0 |
| 18 | 13.0 |
| 19 | 1.3 |
| 20 | 5.2 |
| 27 | 3.0 |
| 31 | 5.6 |
| 36 | 1.6 |
| 37 | 1.1 |
| 41 | 2.8 |
| 42 | 6.1 |
| 43 | 6.0 |
| 46 | 13.0 |
| 47 | 7.8 |
| 48 | 16.0 |
| 49 | 13.0 |
| 50 | 17.0 |
| 60 | 11.0 |

Processes for preparing dihydropyrimidine derivatives represented by the formulae (2a) and (2b) which are tautomeric isomers are shown in the following preparations.

PREPARATION 1

5-Ethoxycarbonyl-2,6-dimethyl-4-phenyl-dihydropyrimidine 625 ml of 5-Ethoxycarbonyl-6-hydroxy-2,6-dimethyl-4-phenyl-1,4,5,6-tetrahydropyrimidine was dissolved in 5 ml of anhydrous benzene and 472 mg of para-toluene sulfonic acid was added and refluxed for 1.5 hrs.

Almost benzene was removed by distillation and the residue was diluted with saturated aqueous potassium carbonate solution and extracted with chloroform. The organic layer was dried over anhydrous potassium carbonate and then the solvent was removed by distillation under reduced pressure to obtain 572 mg of the residue. It was subjected to alumina (Wako Junyaku K.K.) column chromatography and eluted with a mixture of chloroform/benzene 1:1 and then chloroform to obtain 398 mg of title compound. The compound was dissolved in ethanol and treated with saturated etheric HCl solution to obtain a HCl salt of title dihydropyrimidine.

Properties: Colorless crystals m.p.: 156°–157° (Recrystallization from ether/hexane)

IR spectrum ($CHCl_3$, $cm^{-1}$): 3440, 1695

$^1$H-NMR spectrum (DMSO-$d_6$, ppm): 1.08 (3H, t, J=7 Hz), 1.86 (3H, s), 2.20 (3H, s), 3,96 (2H, q, J=7 Hz), 5.33 (1H, s), 7.15–7.30 (5H, m)

Properties of HCl salt:

m.p.: 209°–211° (Recrystallization from ethanol/ether)

Analysis: Caluculated for $C_{15}H_{19}ClN_2O_2$: C, 61.12; H, 6.50; N, 9.50 (%). Found: C, 61.14; H, 6.52; N, 9.34 (%).

By the methods of Examples 18(b) and 19(a), dihydropyrimidine derivatives of the formula (2a) or (2b) shown in Table 6 were produced in Preparations 2–8 by using diketene.

TABLE 6

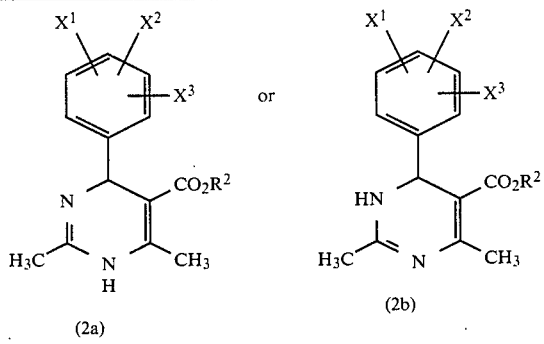

(2a) or (2b)

| Preparation No. | Compound | Overall yield (%) from diketene | Properties | IR spectrum ($CHCl_3$, $cm^{-1}$) | NMR spectrum ($CDCl_3$, δ ppm) | High resolution mass spectrum |
|---|---|---|---|---|---|---|
| 2 | $R^2$=methylbenzyl-aminoethyl $X^1$=2-nitro $X^2$=$X^3$=H | 44 | oil | 3410, 1690, 1610 | 2.02(3H,s), 2.05(3H,s), 2.44(2H, t,J=6Hz), 2.46(3H,s), 3.35(2H,d, J=14Hz), 3.42(2H,d,J=14Hz), 4.05(2H,t,J=6Hz), 5.98(1H,s), 7.20–7.85(4H,m) | Calculated for $C_{23}H_{26}N_4O_4$: 422.1951 Found: 422.1940 |
| 3 | $R^2$=2-methoxyethyl $X^1$=2-nitro $X^2$=$X^3$=H | 18 | oil | 3410, 1690, 1610 | 1.90(3H,s), 2.33(3H,s), 3.18 (3H,s), 3.32(2H,t,J=5Hz), 4.00(2H,t,J=5Hz), 6.00(1H,s), 7.20–7.85(4H,m) | Calculated for $C_{16}H_{19}N_3O_5$: 333.3456 Found: 333.3462 |
| 4 | $R^2$=2-phenoxyethyl $X^1$=2-nitro $X^2$=$X^3$=H | 3 | oil | 3425, 1700, 1600 | 2.01(3H,s), 2.46(3H,s), 3.80–4.00(2H,m), 4.08–4.20(2H,m), 5.98(1H,s), 6.70–7.75(4H,m) | Calculated for $C_{21}H_{21}N_3O_5$: 395.1479 Found: 395.1468 |
| 5 | $R^2$=cyclopropylmethyl $X^1$=2-nitro | 27 | m.p. 124–126° | 3420, 1695, 1610 | −0.13–0.15(2H,m), 0.25–0.50(2H, m), 0.70–0.90(1H,m), 1.99(3H,s), | Calculated for $C_{17}H_{19}N_3O_4$: 329.1376 |

TABLE 6-continued

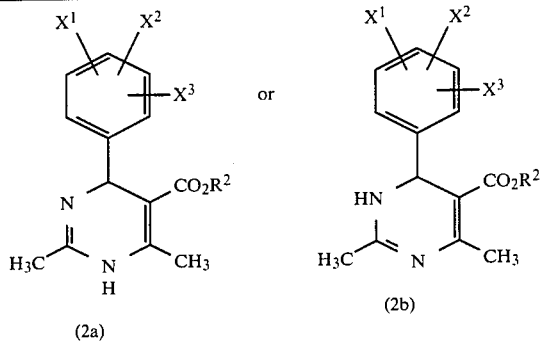

(2a) or (2b)

| Preparation No. | Compound | Overall yield (%) from diketene | Properties | IR spectrum (CHCl$_3$, cm$^{-1}$) | NMR spectrum (CDCl$_3$, δ ppm) | High resolution mass spectrum |
|---|---|---|---|---|---|---|
| | $X^2=X^3=H$ | | (ethyl-acetate-hexane) | | 2.42(3H,s), 3.69(2H,d,J=7Hz), 6.00(1H,s), 7.30–7.80(4H,m) | Found: 329.1376 |
| 6 | $R^2$=cyclopropylmethyl $X^1$=2-chloro $X^2=X^3=H$ | 13 | oil | 3400, 1690, 1670, 1610 | 0.00–0.15(2H,m), 0.30–0.45(2H,m), 0.85–1.00(1H,m), 1.94(3H,s), 2.43(3H,s), 3.77(2H,d,J=7Hz), 6.00(1H,s), 7.15–7.40(4H,m) | Calculated for C$_{17}$H$_{19}$ClN$_2$O$_2$: 318.8049 Found: 318.8040 |
| 7 | $R^2$=cyclopropylmethyl $X^1$=2-bromo $X^2=X^3=H$ | 36 | oil | 3420, 1695 | −0.40–0.50(4H,m), 0.80–1.10(1H, m), 1.87(3H,s), 2.39(3H,brs), 3.77(2H,d,J=7Hz), 5.10–5.80(1H, m), 5.97(1H,s), 6.90–7.70(4H,m) | Calculated for C$_{17}$H$_{19}$BrN$_2$O$_2$: 363.2559 Found: 363. 2563 |
| 8 | $R^2$=cyclopropylmethyl $X^1$=3-nitro $X^2=X^3=H$ | 70 | oil | 3430, 1700 | 0.13–0.50(4H,m), 0.98–1.10(1H,m), 2.04(3H,s), 2.36(3H,s), 3.80–3.90(2H,m), 5.69(1H,s), 7.43–8.16(4H,m) | Calculated for C$_{17}$H$_{19}$N$_3$O$_4$: 329.1376 Found: 329.1374 |

PREPARATION 9

5-n-Butyloxycarbonyl-2,6-dimethyl-4-(2-chloro)-phenyldihydropyrimidine 12 g of t-Butoxypotassium dissolved in 50 ml of dimethylformamide was added to a solution of 13 g of acetamidine hydrochloride in 100 ml of dimethylformamide with stirring at 0° C. Then a solution of 28 g of n-butyl 2-acetyl-3-(2-chloro)phenyl-2-propenoate in 50 ml of dimethyl formamide was added dropwise. After 30 minutes, 40 g of paratoluene sulfonic acid monohydrate was added to the reaction mixture and the mixture was heated at 100°–120° C. for 2 hrs. The reaction solution was made alkaline with NaOH and extracted with 200 ml of ether×4 and the organic layer was twice washed with water and dried over anhydrous magnesium sulfate. The solvent was removed by distillation under reduced pressure. 31.6 g of the residue was purified on silica gel (500 g of SiO$_2$) by chromatography and eluted with 3–10% methanol/chloroform to obtain 24 g (75% yield) of title compound as crystals.

Physicochemical data of the product are shown in Table 7.

By the method of Preparation 9, dihydropyrimidine derivatives of the formula (2a) or (2b) were obtained by using diketene in Preparations 10–20. Yield data and physicochemical data of the products are also shown in Table 7.

TABLE 7

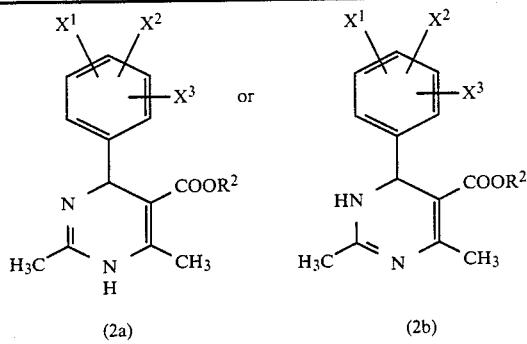

(2a) or (2b)

| Preparation No. | (2a) or (2b) | Yield (%) | Properties (Recrystallization solvents) | IR spectrum (CHCl$_3$, cm$^{-1}$) | NMR spectrum (CDCl$_3$, δ ppm, 270 MHz) | High resolution mass spectrum |
|---|---|---|---|---|---|---|
| 9 | $X^1$=2-chloro $X^2=X^3=H$ $R^2$=n-butyl | 75 | m.p. 90–95° (benzene. | 3430, 1700 | 0.78(3H,t,J=7Hz), 1.05–1.14(2H,m), 1.37–1.47(2H,m), 1.80(3H,s) 2.33(3H,s), 3.85–4.01(2H,m), | Calculated for C$_{17}$H$_{21}$ClN$_2$O$_2$: 320.8207 Found: 320.8186 |

TABLE 7-continued

Structures (2a) and (2b): substituted phenyl with $X^1$, $X^2$, $X^3$; (2a) has NH in ring with $H_3C$–C=N–H and C=C(CH$_3$)COOR$^2$; (2b) has exocyclic HN with $H_3C$–C=N and C=C(CH$_3$)COOR$^2$.

| Preparation No. | (2a) or (2b) | Yield (%) | Properties (Recrystallization solvents) | IR spectrum (CHCl$_3$, cm$^{-1}$) | NMR spectrum (CDCl$_3$, δ ppm, 270 MHz) | High resolution mass spectrum |
|---|---|---|---|---|---|---|
| 10 | $X^1$=2-nitro<br>$X^2$=$X^3$=H<br>$R^2$=isopropyl | 81 | hexane)<br>m.p. 129–132°<br>(chloroform. hexane) | 3410, 1690 | 5.97(1H,s), 7.12–7.34(4H,m)<br>0.76(3H,d,J=6Hz), 1.08(3H,d, J=6Hz), 1.98(3H,s), 2.43(3H,s), 4.77–4.86(1H,m), 5.92(1H,s), 6.50(1H,br), 7.37–7.85(4H,m) | Calculated for C$_{16}$H$_{19}$N$_3$O$_4$: 317.3462<br>Found: 317.3490 |
| 11 | $X^1$=2-nitro<br>$X^2$=$X^3$=H<br>$R^2$=n-propyl | 62 | m.p. 146–148°<br>(benzene. hexane) | 3410, 1690 | 0.66(3H,t,J=7Hz), 1.30–1.50(2H,m), 2.00(3H,s), 2.46(3H,s), 3.75–3.95(2H,m), 5.97(1H,s), 7.30–7.95(4H,m) | Calculated for C$_{16}$H$_{19}$N$_3$O$_4$: 317.3462<br>Found: 317.3492 |
| 12 | $X^1$=2-nitro<br>$X^2$=$X^3$=H<br>$R^2$=isobutyl | 85 | colorless oil | 3430, 1700 | 0.65(3H,d,J=7Hz), 0.67(3H,d, J=7Hz), 1.63–1.73(1H,m), 1.96 (3H,s), 2.43(3H,s), 3.62–3.75 (2H,m), 6.01(1H,s), 7.37–7.85(4H,m) | Calculated for C$_{17}$H$_{21}$N$_3$O$_4$: 331.3732<br>Found: 331.3740 |
| 13 | $X^1$=2-nitro<br>$X^2$=$X^3$=H<br>$R^2$=sec-butyl | 47 | colorless oil | 3440, 1705 | 0.36, 0.78(each 3H,t,J=7Hz), 0.72, 1.07(each 3H,t,J=6Hz), 1.10–1.30, 1.30–1.50(each 2H,m), 1.98(3H×2,s), 2.43, 2.45(each 3H, s), 4.60–4.80(1H×2,m), 5.94, 5.97 (each 1H,s), 7.30–7.95(4H×2,m) | Calculated for C$_{17}$H$_{21}$N$_3$O$_4$: 331.3732<br>Found: 331.3760 |
| 14 | $X^1$=2-nitro<br>$X^2$=$X^3$=H<br>$R^2$=3,3-dimethylbutyl | 57 | colorless oil | 3410, 1690, 1610 | 0.80(9H,s), 1.28(2H,t,J=6Hz), 1.99(3H,s), 2.43(3H,s), 3.95(2H,t,J=6Hz), 5.97(1H,s), 7.35–7.85(4H,m) | Calculated for C$_{19}$H$_{25}$N$_3$O$_4$: 359.1842<br>Found: 359.1835 |
| 15 | $X^1$=3-trifluoromethyl<br>$X^2$=$X^3$=H<br>$R^2$=n-pentyl | 52 | colorless oil | 3430, 1690, 1655 | 0.83(3H,t,J=7Hz), 1.10–1.60(6H,m), 1.94(3H,s), 2.32(3H,s), 4.00(2H,m), 5.57(1H,s), 7.38–7.70(4H,m) | Calculated for C$_{19}$H$_{23}$F$_3$N$_2$O$_2$: 368.4010<br>Found: 368.4039 |
| 16 | $X^1$=4-methylthio<br>$X^2$=$X^3$=H<br>$R^2$=2-ethylbutyl | 80 | colorless oil | 3420, 1700, 1630 | 0.78(6H,m), 1.17(4H,m), 1.38(1H,m), 1.92(3H,s), 2.34(3H,s), 2.47(3H,s), 3.92(2H,d), 5.00(1H,br), 5.46(1H,s), 7.16–7.27(4H,m) | Calculated for C$_{20}$H$_{28}$N$_2$O$_2$S: 360.5204<br>Found: 360.5188 |
| 17 | $X^1$=2-bromo<br>$X^2$=$X^3$=H<br>$R^2$=n-pentyl | 72 | colorless oil | 3420, 1690 | 0.79(3H,t,J=7Hz), 0.90–1.50(6H,m), 1.94(3H,s), 2.44(3H,brs), 3.94(2H,m), 5.94(1H,brs), 7.05–7.60(4H,m) | Calculated for C$_{18}$H$_{23}$BrN$_2$O$_2$: 379.2986<br>Found: 379.3001 |
| 18 | $X^1$=2-nitro<br>$X^2$=$X^3$=H<br>$R^2$=n-heptyl | 82 | colorless oil | 3400, 1685 | 0.86(3H,t,J=7Hz), 0.85–1.50 (10H,m), 1.97(3H,s), 2.43(3H,s), 3.75–4.05(2H,m), 5.98(1H,s), 7.30–8.00(4H,m) | Calculated for C$_{20}$H$_{27}$N$_3$O$_4$: 373.4540<br>Found: 373.4561 |
| 19 | $X^1$=$X^2$=$X^3$=methoxy<br>$R^2$=3-methyl-2-butenyl | 32 | colorless oil | 3430, 1695 | 1.61(3H,s), 1.70(3H,s), 1.98(3H,s), 2.33(3H,s), 3.80(9H,s), 4.45–4.60(2H,m), 5.24(1H,t,J=7Hz), 5.46(1H,s), 6.54(2H,s) | Calculated for C$_{21}$H$_{28}$N$_2$O$_5$: 388.4658<br>Found: 388.4641 |
| 20 | $X^1$=3-cyano<br>$X^2$=$X^3$=H<br>$R^2$=2-cyclopentylethyl | 75 | colorless oil | 3420, 2225, 1690 | 0.90–1.85(11H,m), 1.98(3H,s), 2.34(3H,s), 3.95–4.15(2H,m), 5.57(1H,s), 7.35–7.75(4H,m) | Calculated for C$_{21}$H$_{25}$N$_3$O$_2$: 351.4506<br>Found: 351.4533 |

As clearly shown in Table 5, the compounds of this invention have strong vasodilative effects and the effects endure over a long period. This makes the compounds useful as vasodilators, agents for improving brain circulation and hypotensive agents. By administering the compound of this invention at a lower dose level and at long intervals the above diseases can be effectively treated and the side effects of the compound of this invention are then minimized. Therefore, treatment of the above diseases with the compound of this invention can be simply and safely maintained over a long period.

What is claimed is:

1. A 2,6-dimethyl-3N,5-disubstituted-4-(substituted phenyl) 3,4-dihydropyrimidine compound of the formula:

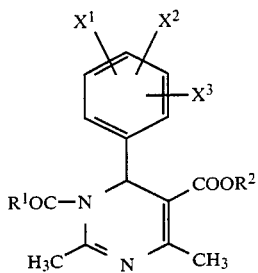

wherein $X^1$, $X^2$ and $X^3$ are the same or different and are hydrogen, nitro, Br, F, Cl, cyano, trifluoromethyl, methylthio or lower alkoxy, with the proviso that when one of $X^1$, $X^2$ and $X^3$ is nitro or cyano, the remainder are other than nitro and cyano;

$R^1$ is ($C_1$–$C_{13}$) straight or branched alkoxy,
($C_4$–$C_{12}$) straight or branched alkenyloxy,
($C_5$–$C_8$) straight or branched alkynyloxy,
($C_1$–$C_4$) straight or branched alkyl,
($C_3$–$C_6$) cycloalkyl,
—O—$(CH_2)_n$—A wherein n is 1, 2 or 3, A is cyclopropyl, cyclobutyl, cyclopentyl or ($C_1$–$C_3$) haloalkyl,
—O—$(CH_2)_m$—O—B wherein m is 1, 2, 3 or 4, B is ($C_1$–$C_3$) alkyl, or
—O—$(CH_2)_l$—D wherein l is an integer from zero to 8, D is phenyl or substituted phenyl;

$R^2$ is ($C_1$–$C_{12}$) straight or branched alkyl,
—$(CH_2)_p$—E wherein p is 1, 2 or 3, E is cyclopropyl, cyclobutyl or cyclopentyl,
($C_4$–$C_7$) straight or branched alkenyl,

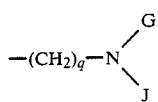

wherein q is 2, 3 or 4, G and J are the same or different and are phenyl, methyl, ethyl, isopropyl-benzyl, phenethyl, methoxycarbonyl or ethoxycarbonyl, or —$(CH_2)_r$—O—L wherein r is 1 or 2, L is methyl, ethyl or phenyl, with the proviso that when $R^1$ is methoxy or ethoxy, $R^2$ is neither methyl nor ethyl, or pharmaceutically acceptable acid addition salts of said compound.

2. A compound according to claim 1, wherein $X^1$, $X^2$ and $X^3$ are the same or different and are methoxy, ethoxy, propoxy or butoxy.

3. A compound according to claim 1 wherein $R^1$ is ($C_1$–$C_{13}$) straight or branched alkoxy, —O—$(CH_2)_n$—A wherein n is 1, 2 or 3, A is cyclopropyl, cyclobutyl or cyclopentyl,
—O—$(CH_2)_m$—O—B wherein m is 1, 2, 3 or 4, B is ($C_1$–$C_3$) alkyl, or
—O—$(CH_2)_l$—D wherein l is an integer from zero to 8, D is phenyl or substituted phenyl; and $R^2$ is —$(CH_2)_p$—E wherein p is 1, 2 or 3, E is cyclopropyl, cyclobutyl or cyclopentyl,

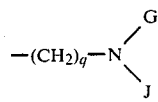

wherein q is 2, 3 or 4, G and J are the same or different and are phenyl, methyl, ethyl, isopropyl, benzyl, phenethyl, methoxycarbonyl or ethoxycarbonyl, or —$(CH_2)_r$—O—L wherein r is 1 or 2, L is methyl, ethyl or phenyl.

4. Compound according to claim 3, wherein D is phenyl, nitrophenyl, chlorophenyl, bromophenyl, methoxycarbonylphenyl, ethoxycarbonylphenyl, propoxycarbonylphenyl, fluorophenyl, dimethoxyphenyl, ethoxyphenyl, trimethoxyphenyl, cyanophenyl or diethoxyphenyl.

5. A compound according to claim 1 or 3 wherein D is phenyl, nitrophenyl, chlorophenyl, bromophenyl, methoxycarbonylphenyl, ethoxycarbonylphenyl, propoxycarbonylphenyl, fluorophenyl, dimethoxyphenyl, methoxyphenyl, trimethoxyphenyl, cyanophenyl or diethoxyphenyl.

6. A compound according to claim 1 wherein $R^1$ is ($C_1$–$C_{13}$) straight or branched alkoxy, —O—$(CH_2)_n$—A wherein n is 1, 2 or 3, A is cyclopropyl, cyclobutyl, cyclopentyl or ($C_1$–$C_3$) haloalkyl,
—O—$(CH_2)_m$—O—B wherein m is 1, 2, 3 or 4, B is ($C_1$–$C_3$) alkyl, or
—O—$(CH_2)_l$—D wherein l is an integer from zero to 8, D is phenyl or substituted phenyl; and $R^2$ is methyl or ethyl.

7. A compound according to claim 6 wherein D is phenyl, nitrophenyl, chlorophenyl, bromophenyl, fluorophenyl, methoxyphenyl or dimethoxyphenyl.

8. A compound according to claim 1 wherein $R^1$ is ($C_1$–$C_{13}$) straight or branched alkoxy, ($C_4$–$C_{12}$) straight or branched alkenyloxy, ($C_5$–$C_8$) straight or branched alkynyloxy, —O—$(CH_2)_n$—A wherein n is 1, 2 or 3, A is cyclopropyl, cyclobutyl or cyclopentyl or
—O—$(CH_2)_l$—D wherein l is an integer from zero to 8, D is phenyl or substituted phenyl; and $R^2$ is ($C_3$–$C_{12}$) straight or branched alkyl, ($C_4$–$C_7$) straight, or branched alkenyl or —$(CH_2)_p$—E wherein p is 1, 2 or 3, E is cyclopropyl, cyclobutyl or cyclopentyl.

9. A compound according to claim 8 wherein D is phenyl, nitrophenyl, chlorophenyl, bromophenyl, methoxycarbonylphenyl, ethoxycarbonylphenyl, propoxycarbonylphenyl, fluorophenyl, dimethoxyphenyl, methoxyphenyl, trimethoxyphenyl, cyanophenyl or diethoxyphenyl.

10. A compound according to claim 1 wherein $R^1$ is ($C_1$–$C_4$) straight or branched alkyl or ($C_3$–$C_6$) cycloalkyl and $R^2$ is methyl or ethyl.

11. A composition for treating disorders of the cardiovascular system comprising 2,6-dimethyl-3N,5-disubstituted-4-(substituted phenyl) 3,4-dihydropyrimidine compound(s) of the formula:

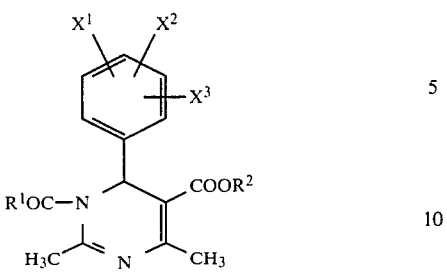

wherein
X$^1$, X$^2$ and X$^3$ are the same or different and are hydrogen, nitro, Br, F, Cl, cyano, trifluoromethyl, methylthio or lower alkoxy, with the proviso that when one of X$^1$, X$^2$ and X$^3$ is nitro or cyano, the remainder are other than nitro and cyano;
R$^1$ is
(C$_1$-C$_{13}$) straight or branched alkoxy,
(C$_4$-C$_{12}$) straight or branched alkenyloxy,
(C$_5$-C$_8$) straight or branched alkynyloxy,
(C$_1$-C$_4$) straight or branched alkyl,
(C$_3$-C$_6$) cycloalkyl,
—O—(CH$_2$)$_n$—A wherein n is 1, 2 or 3, A is cyclopropyl, cyclobutyl, cyclopentyl or (C$_1$-C$_2$) haloalkyl, ,
—O—(CH$_2$)$_m$—O—B wherein m is 1, 2, 3 or 4, B is (C$_1$-C$_3$) alkyl, or
—O—(CH$_2$)$_l$—D wherein l is an integer from zero to 8, D is phenyl or substituted phenyl;
R$^2$ is
(i) (C$_1$-C$_{12}$) straight or branched alkyl,
(ii) (C$_4$-C$_7$) straight or branched alkenyl,
(iii) —(CH$_2$)$_p$—E wherein p is 1, 2 or 3, E is cyclopropyl, cyclobutyl or cyclopentyl,
(iv)

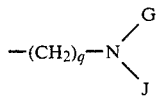

wherein q is 2, 3 or 4, G and J are the same or different and are phenyl, methyl, ethyl, isopropyl, benzyl, phenethyl, methoxycarbonyl or ethoxycarbonyl, or
(v) —(CH$_2$)$_r$—O—L wherein r is 1 or 2, L is methyl, ethyl or phenyl,
with the proviso that when R$^1$ is methoxy or ethoxy, R$^2$ is neither methyl nor ethyl, or a pharmaceutically acceptable acid addition salt of said compound; and a pharmaceutically acceptable carrier.

12. A method for treating disorders of the cardiovascular system in a mammal comprising administering an effective amount of a 2,6-dimethyl-3N,5-disubstituted-4-(substituted phenyl) 3,4-dihydropyrimidine compound of the formula:

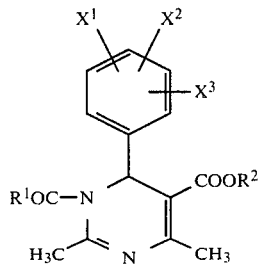

wherein
X$^1$, X$^2$ and X$^3$ are the same or different and are hydrogen, nitro, Br, F, Cl, cyano, trifluoromethyl, methylthio or lower alkoxy, with the proviso that when one of X$^1$, X$^2$ and X$^3$ is nitro or cyano, the remainder are other than nitro and cyano;
R$^1$ is
(C$_1$-C$_{13}$) straight or branched alkoxy,
(C$_4$-C$_{12}$) straight or branched alkenyloxy,
(C$_5$-C$_8$) straight or branched alkynyloxy,
(C$_1$-C$_4$) straight or branched alkyl,
(C$_3$-C$_6$) cycloalkyl,
—O—(CH$_2$)$_n$—A wherein n is 1, 2 or 3, A is cyclopropyl, cyclobutyl, cyclopentyl or (C$_1$-C$_3$) haloalkyl,
—O—(CH$_2$)$_m$—O—B wherein m is 1, 2, 3 or 4, B is (C$_1$-C$_3$) alkyl, or
—O—(CH$_2$)$_l$—D wherein l is an integer from zero to 8, D is phenyl or substituted phenyl;
R$^2$ is
(i) (C$_1$-C$_{12}$) straight or branched alkyl,
(ii) (C$_4$-C$_7$) straight or branched alkenyl,
(iii) —(CH$_2$)$_p$—E wherein p is 1, 2 or 3, E is cyclopropyl, cyclobutyl or cyclopentyl,
(iv)

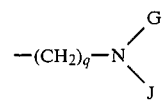

wherein q is 2, 3 or 4, G and J are the same or different and are phenyl, methyl, ethyl, isopropyl, benzyl, phenethyl, methoxycarbonyl or ethoxycarbonyl, or
(v) —(CH$_2$)$_r$—O—L wherein r is 1 or 2, L is methyl, ethyl or phenyl,
with the proviso that when R$^1$ is methoxy or ethoxy, R$^2$ is neither methyl nor ethyl, or a pharmaceutically acceptable acid addition salt of said compound to said mammal.

13. The method according to claim 12, wherein D is phenyl, nitrophenyl, chlorophenyl, bromophenyl, methoxycarbonylphenyl, ethoxycarbonylphenyl, propoxycarbonylphenyl, fluorophenyl, dimethoxyphenyl, methoxyphenyl, trimethoxyphenyl, cyanophenyl or diethoxyphenyl.

* * * * *